United States Patent
Sarkar et al.

(10) Patent No.: US 10,017,531 B2
(45) Date of Patent: Jul. 10, 2018

(54) LIPID-BASED PLATINUM-N-HETEROCYCLIC CARBENE COMPOUNDS AND NANOPARTICLES

(71) Applicant: INVICTUS ONCOLOGY PVT. LTD., Delhi (IN)

(72) Inventors: Arindam Sarkar, Delhi (IN); Swadhin Kumar Mandal, Kolkata Mohanpur (IN)

(73) Assignee: INVICTUS ONCOLOGY PVT. LTD., Delhi (IN)

( * ) Notice: Subject to any disclaimer, the term of this patent is extended or adjusted under 35 U.S.C. 154(b) by 0 days.

(21) Appl. No.: 14/897,565

(22) PCT Filed: Jun. 13, 2014

(86) PCT No.: PCT/IB2014/062210
§ 371 (c)(1),
(2) Date: Dec. 10, 2015

(87) PCT Pub. No.: WO2014/199352
PCT Pub. Date: Dec. 18, 2014

(65) Prior Publication Data
US 2016/0122377 A1 May 5, 2016

(30) Foreign Application Priority Data

Jun. 14, 2013 (IN) .......................... 1781/DEL/2013

(51) Int. Cl.
*C07F 15/00* (2006.01)
*C07H 23/00* (2006.01)
*C07J 41/00* (2006.01)

(52) U.S. Cl.
CPC ...... *C07F 15/0093* (2013.01); *C07F 15/0086* (2013.01); *C07H 23/00* (2013.01); *C07J 41/0055* (2013.01)

(58) Field of Classification Search
USPC ........................................ 514/183, 184, 185
See application file for complete search history.

(56) References Cited

U.S. PATENT DOCUMENTS

| 3,783,049 A | 1/1974 | Sandera |
| 8,247,574 B2 * | 8/2012 | Straβner ............... C09K 11/06 548/103 |
| 2008/0064895 A1 * | 3/2008 | Du Perez ............ C07F 15/0093 556/137 |

OTHER PUBLICATIONS

Unger (Journal of organometallic chemistry; 713, 2012, 203-208).*
Kim et al. "Size-Selective Synthesis of Gold and Platinum Nanoparticles Using Novel Thiol-Functionalized Ionic Liquids" Langmuir 20:556-560 (2004).
PubChem. Compound Summary for: CID 26031. Create Date Mar. 27, 2005 [retreived from internet on Dec. 15, 2014] <http://pubchem.ncbi.nlm.nih.gov/compound/26031> entire document.
PubChem. Compound Summary for: CID 421887. Create Date Mar. 26, 2005 [retreived from internet on Dec. 15, 2014] <http://pubchem.ncbi.nlm.nih.gov/compound/421887> entire document.
PubChem. Compound Summary for: CID 61859. Create Date Aug. 8, 2005 [retreived from internet on Dec. 15, 2014] <http://pubchem.ncbi.nlm.nih.gov/compound/61859> entire document.
Schuster et al., "Beyond Conventional N-Heterocyclic Carbenes: Abnormal, Remote, and Other Classes of NHC Ligands with Reduced Heteroatom Stabilization", Chem. Rev. 109(8):3445-3478 (2009).

* cited by examiner

*Primary Examiner* — Pancham Bakshi
(74) *Attorney, Agent, or Firm* — Nixon Peabody LLP; David S. Resnick; Ravinderjit Braich

(57) ABSTRACT

The present disclosure is in relation to the field of nanotechnology and cancer therapeutics. In particular, the present disclosure relates to carbene compounds, particularly platinum containing carbenes and corresponding nanoparticles thereof. The disclosure further relates to synthesis of said platinum containing carbenes, nanoparticles and compositions comprising said platinum containing carbenes/nanoparticles. The disclosure also relates to methods of managing cancer by employing aforesaid platinum based compounds, nanoparticles and compositions.

12 Claims, No Drawings

LIPID-BASED PLATINUM-N-HETEROCYCLIC CARBENE COMPOUNDS AND NANOPARTICLES

CROSS REFERENCE TO RELATED APPLICATIONS

This application is a 371 National Phase Entry of International Patent Application No. PCT/IB2014/062210 filed on Jun. 13, 2014 which claims benefit under 35 U.S.C. § 119(a)-119(d) of Indian Patent Application No. 1781/DEL/ 2013 filed Jun. 14, 2013, the contents of which are incorporated herein by reference in their entirety.

TECHNICAL FIELD

The present disclosure is in relation to the field of nanotechnology and cancer therapeutics. In particular, the present disclosure relates to carbene compounds, particularly platinum containing carbenes and corresponding nanoparticles thereof. The disclosure further relates to synthesis of said platinum containing carbenes, nanoparticles and compositions comprising said platinum containing carbenes/nanoparticles. The disclosure also relates to methods of managing cancer by employing aforesaid platinum based compounds, nanoparticles and compositions.

BACKGROUND

Cis-platin, carbo-platin and oxaliplatin are called $1^{st}$, $2^{nd}$ and $3^{rd}$ generation of platinum based anticancer drugs respectively. The $1^{st}$ generation drug Cis-platin is efficacious in many human cancer cell-lines but suffers from the disadvantage of less internalization (thus more doses are needed) and more toxicity issues. The $2^{nd}$ generation drug carboplatin is shown to be accumulated more amount in nucleus than cis-platin due to more internalization but still shows cross-resistance with some of the cis-platin resistant tumors due to the hydrolysis of amino groups after DNA cross linking and also due to the easy recognition of diammineplatinum fragment by DNA repair enzymes. (Ref. Cancer Therapy, 2007, Vol 5, 537-583).

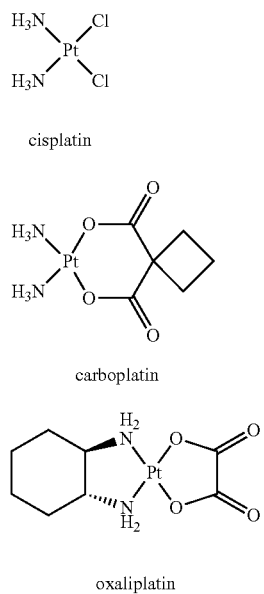

cisplatin carboplatin oxaliplatin

The cellular and molecular aspects of the mechanism of action of the $3^{rd}$ generation drug oxaliplatin have not yet been fully elucidated. However, the intrinsic chemical and steric characteristics of the non-hydrolyzable and hydrophobic diaminocyclohexane (DACH)-platinum adducts on DNA appear to contribute to the lack of cross-resistance with cisplatin and carboplatin. It has been shown recently that attachment of lipids to the cisplatin and oxaliplatin backbone reduces the toxicity of the drugs to a significant extent by formation of nano-particle (EPR effect). (PNAS, 2012, vol. 109, 11294-11299).

The use of nanotechnology in cancer is emerging globally. Although there are few reports on nanoparticles in cancer therapy but all have various drawbacks such as toxicity, low release kinetics of drug, low circulation stability and so on.

Lipid-containing nanoparticles (e.g. Doxil, a pegylated liposomal formulation of doxorubicin hydrochloride) and albumin-complexes (e.g. Abraxane, a paclitaxel-albumin complex) nanoparticles are used in humans and have been demonstrated as having improved systemic toxicity profile and have helped resolve certain formulation challenges (Ferrari M, Nature Rev. Cancer, 2005, 5:161). Platinum-based chemotherapeutic agents are used as first line of therapy in over 70% of all cancers. Cisplatin undergoes rapid formation of cis-$[Pt(NH_3)_2Cl(OH_2)]^+$ and cis-$[Pt(NH_3)_2(OH_2)]^{2+}$ resulting in nephrotoxicity. Further, aquation of both carboplatin and oxaliplatin are significantly slower, resulting in decreased potency. In the recent past, considerable progress has been made wherein, Dhar et al (PNAS, 2008, 105, 17356) generated a platinum (IV) complex (c,t,c-$[Pt(NH_3)_2(O_2CCH_2CH_2CH_2CH_2CH_3)_2Cl_2]$ that is hydrophobic enough for encapsulation into PLGA-b-PEG nanoparticles. However, the prodrug in this case has to be intracellularly processed into cisplatin. Furthermore, alternative strategies based on conjugation of platinum to polymers (eg a polyamidoamine dendrimer-platinum complex) resulted in a 200-550 fold reduction in cytotoxicity than free cisplatin. This was a result of strong bonds formed between the polymer and platinum (J Pharm Sci, 2009, 98, 2299). Another example is AP5280, a N-(2-hydroxypropyl) methacrylamide copolymer-bound platinum that is less potent than carboplatin. Here, the platinum is held by an aminomalonic acid chelating agent coupled to the COOH-terminal glycine of a tetrapeptide spacer (Clin Can Res, 2004, 10, 3386; Eur J Can, 2004, 40, 291).

Further, WO 2010/091192 A2 (Sengupta et al.) discloses biocompatible conjugated polymer nanoparticles including a copolymer backbone, a plurality of sidechains covalently linked to said backbone, and a plurality of platinum compounds dissociably linked to said backbone. The disclosure is further directed to dicarbonyl-lipid compounds wherein a platinum compound is dissociably linked to the dicarbonyl compound.

However, various drawbacks are associated with the presently employed platinum compounds and nanoparticles. The present disclosure aims at overcoming the drawbacks of the prior art and providing for stable, potent and safer platinum compounds and nano-platinates in cancer chemotherapy.

SUMMARY

The disclosure provides synthetic strategies for the preparation of carboplatin and oxaliplatin analogues of NHC platinum complexes by replacing nitrogen containing backbone by NHC; as well as lipid functionalization of cis and trans NHC-platinum complexes. Without wishing to be bound by a theory, these compounds can show comparable or better efficacy and less toxicity than all three generations of anticancer drugs in the form of nanoparticle.

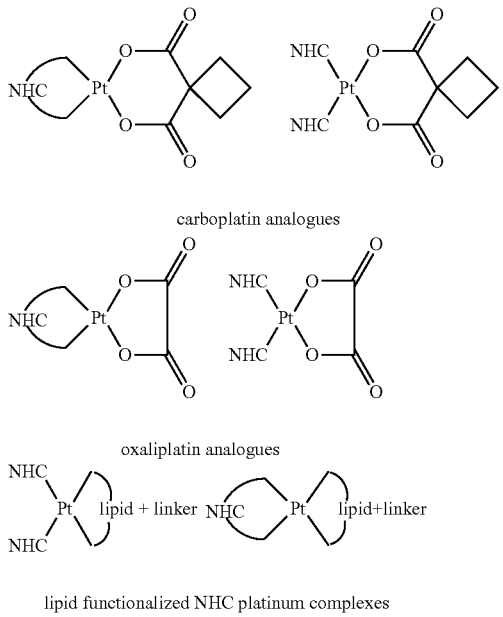

lipid functionalized NHC platinum complexes

In one aspect, the disclosure provides a carbene compound of Formula (VI):

 (VI)

wherein,
$X_1$, $X_2$, $X_3$ and $X_4$ are selected independently from the group consisting of O, P, S, Se, Cl, N, C, O-A, O—B, DACH, halides and chelated or non-chelated dicarboxylato linkage group and any combination thereof,
A and B are independently C, P, S, N, or any combination thereof, and wherein $X_4$, is optional.

In various compounds of Formula (VI) at least one of $X_1$, $X_2$, $X_3$ and $X_4$ is a carbene.

In some embodiments, the platinum containing compound is Pt(II) compound, Pt(IV) compound, or halide containing platinum compound.

In another aspect, the disclosure provides a method for preparing an abnormal N-heterocyclic-carbene platinum(II) compound as described above, said method comprising:
(a) optionally reacting Compound A (e.g. a carboximidamide or a carboximidamide derivative) with phenacyl halide and potassium carbonate to obtain Compound B (a substituted imidazole);
(b) reacting the Compound B of above with reagent selected from a group comprising alkyl halide, dihaloalkane, picolyl halide and 2-halo ethylamine or any combination thereof to obtain Compound C (an imidazolium halide); and
(c) reacting:
(i) the Compound B of above with a reagent selected from a group comprising potassium haloplatinate, sodium acetate, alkyl amine and pyridine to obtain said abnormal N-heterocyclic-carbene platinum(II) compound, and
(ii) optionally, reacting the abnormal N-heterocyclic-carbene platinum(II) compound obtained in above with reagent selected from a group comprising salt of carboxylic acid, salt of cholesterol acid, or cholic acid or deoxycholic acid to obtain substituted abnormal N-heterocyclic-carbene platinum(II) compound, or
(iii) optionally, reacting the abnormal N-heterocyclic-carbene platinum(II) compound obtained as above with a lipid to obtain substituted abnormal N-heterocyclic-carbene platinum(II) compound.

The disclosure also provides particles, such as nanoparticles comprising one or more of the Pt-lipid molecules disclosed herein. Thus, in one aspect, the disclosure provides a particle, for example, but not limited, a nanoparticle comprising a platinum based compound, wherein the platinum based compound comprises a carbene.

The disclosure also provides a pharmaceutical composition comprising the compound as disclosed above or the nanoparticle as disclosed above or a combination thereof, along with pharmaceutically acceptable excipient; and a method of managing or treating cancer, said method comprising step of administering the compound as disclosed above or the nanoparticle as disclosed above or the composition as disclosed above, to a subject in need thereof.

BRIEF DESCRIPTION OF THE DRAWINGS

In order that the invention may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure.

DETAILED DESCRIPTION

In the various embodiments, platinum based compounds are disclosed which comprises a carbene. As used in this disclosure, the term "carbene" refers a carbon atom six total valence electrons where four electrons are shared to form bonds with two other neighboring atoms and where two electrons are present as a lone pair. The lone pair can exist in two states where both electrons in the lone pair are in the same orbital (singlet) or both electrons in the lone pair are found in different orbitals (triplet). In some embodiments, the carbene is a heterocyclic carbene. As used herein, the term "N-heterocyclic carbene" or "NHC" refers to a molecule having a carbene atom present in a heterocyclic ring where at least one of the atoms flanking the carbene carbon is nitrogen. In some embodiments, NHC is an abnormal NHC. As used herein, abnormal NHCs are ligands which bind to metal through an atom which is stabilized by only one adjacent heteroatom. In normal NHC, the atom connected to the metal is stabilized by two adjacent hetero atoms. For example, Compounds 86 and 87 of the disclosure are normal carbenes and all other are abnormal carbenes.

Thus, abnormal NHC is stronger sigma electron donor to metal than normal NHC[ref "Chemical Review 109(8): 3445-3478, 2009"]

Exemplary carbenes include, but are not limited to, cyclic diaminocarbenes, imidazol-2-ylidenes (e.g., 1,3-dimesitylimidazol-2-ylidene and 1,3-dimesityl-4,5-dihydroimidazol-2-ylidene), 1,2,4-triazol-3-ylidenes, and 1,3-thiazol-2-ylidenes. In some embodiments, the carbine is imidazol-2-ylidene or a derivative thereof In some embodiments, the platinum containing carbene compound further comprises a lipid. The lipid can be linked to the platinum atom in the carbene compound either directly or via a linker molecule. In some embodiments, the platinum is linked to the lipid molecule via a linker molecule. For example, the presence of a linker can provide for a carbamate and/or ether linkage connecting a dicarbonyl molecule (for linking with the platinum moiety) and the lipid molecule. In some other embodiments of the present disclosure, the platinum is directly connected to the lipid molecule. All possible linker molecules providing a carbamate and/or ether linkage form a part of the instant disclosure. Accordingly, in some embodiments, at least one (e.g., one, two, or three) of $X_1$, $X_2$, $X_3$, and $X_4$ is a -linker-lipid.

In some embodiments of the various aspects disclosed herein, the platinum is coordinated to a leaving group via a unique O—Pt monocarboxylato covalent bond and a =O→Pt coordinate bond. Further, the present disclosure also discloses platinum based compounds wherein the platinum is co-ordinated to a leaving group via O—Pt monocarboxylato or dicarboxylato covalent bond(s).

In some embodiments of the various aspects disclosed herein, the platinum moiety is a platinum (II) or platinum (IV) compound. In some embodiments, the platinum (II) compound is selected from the group comprising of DACH-platinum, cisplatin, oxaliplatin, carboplatin, paraplatin, sartraplatin, and various combinations thereof. In some embodiments, the platinum containing compound is Pt(II) compound, Pt(IV) compound or halide containing platinum compound. In another exemplary embodiment, the platinum compound is selected from platinum containing carbenes, preferably, abnormal N-heterocyclic-carbene (NHC) platinum(II) complexes.

In some embodiments, the platinum compound comprising the carbene is of Formula (I):

(I)

wherein $R_1$, $R_2$, $R_3$, $R_4$ are independently halogen, alkyl, amino, alkylamino, dialkylamino, hydroxyl, alkoxy, thiol, thioalkyl, O-acyl, chelated or non-chelated dicarboxylato linkage, linker-lipid, O, P, S, Se, Cl, N, C, O-A, O—B, DACH or any combination thereof, wherein A and B are selected independently from the group consisting of C, P, S, N, and any combination thereof, provided that at least one (e.g., one, two, three, or four) of $R_1$, $R_2$, $R_3$, and $R_4$ is a carbene compound and the platinum atom is linked to the carbene atom.

In some embodiments of Formula (I), at least two of $R_1$, $R_2$, $R_3$ and $R_4$ together with the platinum atom form a 5-, 6-, 7-, 8-, or 9-membered ring, which can be optionally substituted with one or more substituents. In some embodiments, $R_1$ and $R_2$ together with the platinum atom form a 5-, 6-, 7-, 8-, or 9-membered ring. In some embodiments, $R_1$ and $R_3$ together with the platinum atom form a 5-, 6-, 7-, 8-, or 9-membered ring. In some embodiments, $R_1$ and $R_4$ together with the platinum atom form a 5-, 6-, 7-, 8-, or 9-membered ring. In some embodiments, $R_2$ and $R_3$ together with the platinum atom form a 5-, 6-, 7-, 8-, or 9-membered ring. In some embodiments, $R_2$ and $R_4$ together with the platinum atom form a 5-, 6-, 7-, 8-, or 9-membered ring. In some embodiments, $R_3$ and $R_4$ together with the platinum atom form a 5-, 6-, 7-, 8-, or 9-membered ring.

In some embodiments, of Formula (I), at least one (e.g., one, two or three) of $R_1$, $R_2$, $R_3$ and $R_4$ is -linker-lipid.

In some embodiments, the platinum compound comprising the carbene is of Formula (II):

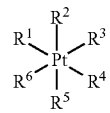

(II)

wherein $R_1$, $R_2$, $R_3$, $R_4$, $R_5$ and $R_6$ are independently halogen, alkyl, amino, alkylamino, dialkylamino, hydroxyl, alkoxy, thiol, thioalkyl, O-acyl, chelated or non-chelated dicarboxylato linkage, -linker-lipid, O, P, S, Se, Cl, N, C, O-A, O—B, DACH or any combination thereof, wherein A and B are selected independently from the group consisting of C, P, S, N, and any combination thereof, provided that at least one (e.g., one, two, three, four or five) of $R_1$, $R_2$, $R_3$, and $R_4$ is a carbene compound and the platinum atom is linked to the carbene atom.

In some embodiments of Formula (II), at least two of $R_1$, $R_2$, $R_3$, $R_4$, $R_5$ and $R_6$ together with the platinum atom form a 5-, 6-, 7-, 8-, or 9-membered ring. In some embodiments, $R_1$ and $R_2$ together with the platinum atom form a 5-, 6-, 7-, 8-, or 9-membered ring. In some embodiments, $R_1$ and $R_3$ together with the platinum atom form a 5-, 6-, 7-, 8-, or 9-membered ring. In some embodiments, $R_1$ and $R_4$ together with the platinum atom form a 5-, 6-, 7-, 8-, or 9-membered ring. In some embodiments, $R_1$ and $R_5$ together with the platinum atom form a 5-, 6-, 7-, 8-, or 9-membered ring. In some embodiments, $R_1$ and $R_6$ together with the platinum atom form a 5-, 6-, 7-, 8-, or 9-membered ring. In some embodiments, $R_2$ and $R_3$ together with the platinum atom form a 5-, 6-, 7-, 8-, or 9-membered ring. In some embodiments, $R_2$ and $R_4$ together with the platinum atom form a 5-, 6-, 7-, 8-, or 9-membered ring. In some embodiments, $R_2$ and $R_5$ together with the platinum atom form a 5-, 6-, 7-, 8-, or 9-membered ring. In some embodiments, $R_2$ and $R_6$ together with the platinum atom form a 5-, 6-, 7-, 8-, or 9-membered ring. In some embodiments, $R_3$ and $R_4$ together with the platinum atom form a 5-, 6-, 7-, 8-, or 9-membered ring. In some embodiments, $R_3$ and $R_5$ together with the platinum atom form a 5-, 6-, 7-, 8-, or 9-membered ring. In some embodiments, $R_3$ and $R_6$ together with the platinum atom form a 5-, 6-, 7-, 8-, or 9-membered ring. In some embodiments, $R_4$ and $R_5$ together with the platinum atom form a 5-, 6-, 7-, 8-, or 9-membered ring. In some embodiments, $R_4$ and $R_6$ together with the platinum atom form a 5-, 6-, 7-, 8-, or 9-membered ring. In some embodiments, $R_5$ and $R_6$ together with the platinum atom form a 5-, 6-, 7-, 8-, or 9-membered ring.

In some embodiments, of Formula (II), at least one (e.g., one, two, three, four or five) of $R_1$, $R_2$, $R_3$, $R_4$, $R_5$ and $R_6$ is -linker-lipid.

The term "lipid" is used in the conventional sense and includes compounds of varying chain length, from as short as about 2 carbon atoms to as long as about 28 carbon atoms. Additionally, the compounds may be saturated or unsaturated and in the form of straight- or branched-chains or in the form of unfused or fused ring structures. Exemplary lipids include, but are not limited to, fats, waxes, sterols, steroids, bile acids, fat-soluble vitamins (such as A, D, E, and K), monoglycerides, diglycerides, phospholipids, glycolipids, sulpholipids, aminolipids, chromolipids (lipochromes), glycerophospholipids, sphingolipids, prenollipids, saccharolipids, polyketides, and fatty acids.

Without limitations the lipid can be selected from the group consisting of sterol lipids, fatty acids, fatty alcohols, glycerolipids (e.g., monoglycerides, diglycerides, and triglycerides), phospholipids, glycerophospholipids, sphingolipids, prenol lipids, saccharolipids, polyketides, and any combination thereof. The lipid can be a polyunsaturated fatty acid or alcohol. The term "polyunsaturated fatty acid" or "polyunsaturated fatty alcohol" as used herein means a fatty acid or alcohol with two or more carbon-carbon double bonds in its hydrocarbon chain. The lipid can also be a highly unsaturated fatty acid or alcohol. The term "highly polyunsaturated fatty acid" or "highly polyunsaturated fatty alcohol" as used herein means a fatty acid or alcohol having at least 18 carbon atoms and at least 3 double bonds. The lipid can be an omega-3 fatty acid. The term "omega-3 fatty acid" as used herein means a polyunsaturated fatty acid whose first double bond occurs at the third carbon-carbon bond from the end opposite the acid group.

In some embodiments, the lipid can be selected from the group consisting of 1,3-Propanediol Dicaprylate/Dicaprate; 10-undecenoic acid; 1-dotriacontanol; 1-heptacosanol; 1-nonacosanol; 2-ethyl hexanol; Androstanes; Arachidic acid; Arachidonic acid; arachidyl alcohol; Behenic acid; behenyl alcohol; Capmul MCM C10; Capric acid; capric alcohol; capryl alcohol; Caprylic acid; Caprylic/Capric Acid Ester of Saturated Fatty Alcohol C12-C18; Caprylic/Capric Triglyceride; Caprylic/Capric Triglyceride; Ceramide phosphorylcholine (Sphingomyelin, SPH); Ceramide phosphorylethanolamine (Sphingomyelin, Cer-PE); Ceramide phosphorylglycerol; Ceroplastic acid; Cerotic acid; Cerotic acid; ceryl alcohol; Cetearyl alcohol; Ceteth-10; cetyl alcohol; Cholanes; Cholestanes; cholesterol; cis-11-eicosenoic acid; cis-11-octadecenoic acid; cis-13-docosenoic acid; cluytyl alcohol; coenzyme Q10 (CoQ10); Dihomo-γ-linolenic; Docosahexaenoic acid; egg lecithin; Eicosapentaenoic acid; Eicosenoic acid; Elaidic acid; elaidolinolenyl alcohol; elaidolinoleyl alcohol; elaidyl alcohol; Erucic acid; erucyl alcohol; Estranes; Ethylene glycol distearate (EGDS); Geddic acid; geddyl alcohol; glycerol distearate (type I) EP (Precirol ATO 5); Glycerol Tricaprylate/Caprate; Glycerol Tricaprylate/Caprate (CAPTEX® 355 EP/NF); glyceryl monocaprylate (Capmul MCM C8 EP); Glyceryl Triacetate; Glyceryl Tricaprylate; Glyceryl Tricaprylate/Caprate/Laurate; Glyceryl Tricaprylate/Tricaprate; glyceryl tripalmitate (Tripalmitin); Henatriacontylic acid; Heneicosyl alcohol; Heneicosylic acid; Heptacosylic acid; Heptadecanoic acid; Heptadecyl alcohol; Hexatriacontylic acid; isostearic acid; isostearyl alcohol; Lacceroic acid; Lauric acid; Lauryl alcohol; Lignoceric acid; lignoceryl alcohol; Linoelaidic acid; Linoleic acid; linolenyl alcohol; linoleyl alcohol; Margaric acid; Mead; Melissic acid; melissyl alcohol; Montanic acid; montanyl alcohol; myricyl alcohol; Myristic acid; Myristoleic acid; Myristyl alcohol; neodecanoic acid; neoheptanoic acid; neononanoic acid; Nervonic; Nonacosylic acid; Nonadecyl alcohol; Nonadecylic acid; Nonadecylic acid; Oleic acid; oleyl alcohol; Palmitic acid; Palmitoleic acid; palmitoleyl alcohol; Pelargonic acid; pelargonic alcohol; Pentacosylic acid; Pentadecyl alcohol; Pentadecylic acid; Phosphatidic acid (phosphatidate, PA); Phosphatidylcholine (lecithin, PC); Phosphatidylethanolamine (cephalin, PE); Phosphatidylinositol (PI); Phosphatidylinositol bisphosphate (PIP2); Phosphatidylinositol phosphate (PIP); Phosphatidylinositol triphosphate (PIP3); Phosphatidylserine (PS); polyglyceryl-6-distearate; Pregnanes; Propylene Glycol Dicaprate; Propylene Glycol Dicaprylocaprate; Propylene Glycol Dicaprylocaprate; Psyllic acid; recinoleaic acid; recinoleyl alcohol; Sapienic acid; soy lecithin; Stearic acid; Stearidonic; stearyl alcohol; Tricosylic acid; Tridecyl alcohol; Tridecylic acid; Triolein; Undecyl alcohol; undecylenic acid; Undecylic acid; Vaccenic acid; α-Linolenic acid; γ-Linolenic acid; a fatty acid salt of 10-undecenoic acid, adapalene, arachidic acid, arachidonic acid, behenic acid, butyric acid, capric acid, caprylic acid, cerotic acid, cis-11-eicosenoic acid, cis-11-octadecenoic acid, cis-13-docosenoic acid, docosahexaenoic acid, eicosapentaenoic acid, elaidic acid, erucic acid, heneicosylic acid, heptacosylic acid, heptadecanoic acid, isostearic acid, lauric acid, lignoceric acid, linoelaidic acid, linoleic acid, montanic acid, myristic acid, myristoleic acid, neodecanoic acid, neoheptanoic acid, neononanoic acid, nonadecylic acid, oleic acid, palmitic acid, palmitoleic acid, pelargonic acid, pentacosylic acid, pentadecylic acid, recinoleaic acid (e.g. zinc recinoleate), sapienic acid, stearic acid, tricosylic acid, tridecylic acid, undecylenic acid, undecylic acid, vaccenic acid, valeric acid, α-linolenic acid, γ-linolenic acid; and any combinations thereof.

In some embodiments, the lipid is cholesterol or alpha tocopherol.

As used herein, the term "linker" means an organic moiety that connects two parts of a compound. Linkers typically comprise a direct bond or an atom such as oxygen or sulfur, a unit such as $NR^1$, C(O), C(O)NH, C(O)O, NHC(O)O, OC(O)O, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $NR^1$, C(O), C(O)NH, C(O)O, NHC(O)O, OC(O)O, $SO_2NH$, cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In some embodiments, the linker is a branched linker. The branchpoint of the branched linker may be at least trivalent, but can be a tetravalent, pentavalent or hexavalent atom, or a group presenting such multiple valencies. In some embodiments, the branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branchpoint is glycerol or derivative thereof.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis. Linkers that contain peptide bonds can be used when targeting cell types rich in peptidases, such as liver cells and synoviocytes.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid celavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleaveable in an acidic environment with a pH of about 6.5 or lower (e.g., about 6.5, 6.0, 5.5, 5.0, or lower), or by agents such as enzymes that can act as a general acid.

Linkers according to the present invention include moieties comprising two or more carbon molecules such as, for example, ethylenediamine, ethyleneglycol, glycine, beta-alanine and polyethylene glycol (PEG) of molecular weight about 44 to about 200 kD. Further, it is to be understood from the present disclosure that the platinum moiety and/or the lipid may be modified to comprise functional groups for linking to the linker molecule.

In some embodiments of the various aspects disclosed herein, the linker is —X—$CH_2$—$X_2$—$X_1$—, wherein X is NH; $X_1$ is C(O)O, C(O)NH, O($CH_2$)—O, NH, or O; $X_2$ is $(CH_2)_n$ or C(O); and n is 0, 1, 2, 3, 4, or 5.

In some other embodiments, the linker is —$(CH_2)_n$O—, —$(CH_2)$—NHC(O)O—, —$(CH_2)_n$OC(O)NH—, —$(CH_2)_n$C(O)NH$(CH_2)_m$O—, —$(CH_2)_n$O$(CH_2)_m$O—, —$(CH_2)_n$O$(CH_2)_m$O—, —$(CH_2)_n$NHC(O)$(CH_2)_m$O—, or —$(CH_2)_n$C(O)O—; and n and m are independently 0, 1, 2, 3, 4, or 5.

In still some other embodiments, the linker is —$X_3$—$X_4X_5$—$X_6$—, wherein $X_3$ is CH, $CH_2$, or O; and $X_4$, $X_5$ and $X_6$ are independently same or different and are —$CH_2$O— or O.

In yet some other embodiments, the linker is —$CH_2$O—.

In some embodiments, the linker is selected from the group consisting of a bond, —O—, NHCH$_2$CH$_2$NHC(O)—, —NHCH$_2$CH$_2$NHC(O)O—, —NHCH$_2$CH$_2$—, —NHCH$_2$CH$_2$O—, —NHCH$_2$C(O)—, —NHCH$_2$C(O)O—, —NHCH$_2$C(O)OCH$_2$CH$_2$CH$_2$—, —NHCH$_2$C(O)OCH$_2$CH$_2$CH$_2$O—, —NHCH$_2$C(O)NH—, —CH$_2$CH$_2$—, —CH$_2$CH$_2$O—, —CH$_2$CH$_2$NHC(O)—, —CH$_2$CH$_2$NHC(O)O—, —CH$_2$CH$_2$O—, —CH$_2$C(O)NHCH$_2$CH$_2$—, —CH$_2$C(O)NHCH$_2$CH$_2$O—, —CH$_2$CH$_2$OCH$_2$CH$_2$—, —CH$_2$CH$_2$OCH$_2$CH$_2$O—, —CH$_2$C(O)—, —CH$_2$C(O)O—, —CH$_2$CH$_2$CH$_2$—, —CH$_2$CH$_2$CH$_2$O—, =CH—CH=CH$_2$—, =CH—CH=CHCH$_2$O—, —CH=CHCH$_2$—, —CH=CHCH$_2$O—, —OCH$_2$CH$_2$O—, —CH$_2$—, —CH$_2$O—, —NHC(O)CH$_2$—, —NHC(O)CH$_2$O—, —C(O)CH$_2$—, —C(O)CH$_2$O—, —OC(O)CH$_2$—, —OC(O)CH$_2$O—, —C(O)CH$_2$CH$_2$C(O)NHCH$_2$CH$_2$—, —OC(O)CH$_2$CH$_2$C(O)NHCH$_2$CH$_2$—, —C(O)CH$_2$CH$_2$C(O)NHCH$_2$CH$_2$O—, —OC(O)CH$_2$CH$_2$C(O)NHCH$_2$CH$_2$O—, —C(O)CH$_2$CH$_2$C(O)NHCH$_2$CH$_2$NHC(O)—, —OC(O)CH$_2$CH$_2$C(O)NHCH$_2$CH$_2$NHC(O)—, —C(O)CH$_2$CH$_2$C(O)NHCH$_2$CH$_2$NHC(O)O—, —OC(O)CH$_2$CH$_2$C(O)NHCH$_2$CH$_2$NHC(O)O—, and any combinations thereof.

In some embodiments, the platinum based compounds disclosed herein are represented by Formula (VI).

In some embodiments, Formula VI represents normal (86 and 87) or abnormal N-heterocyclic-carbene (NHC) platinum(II) complexes [Compounds 88-94]:

Compounds 86

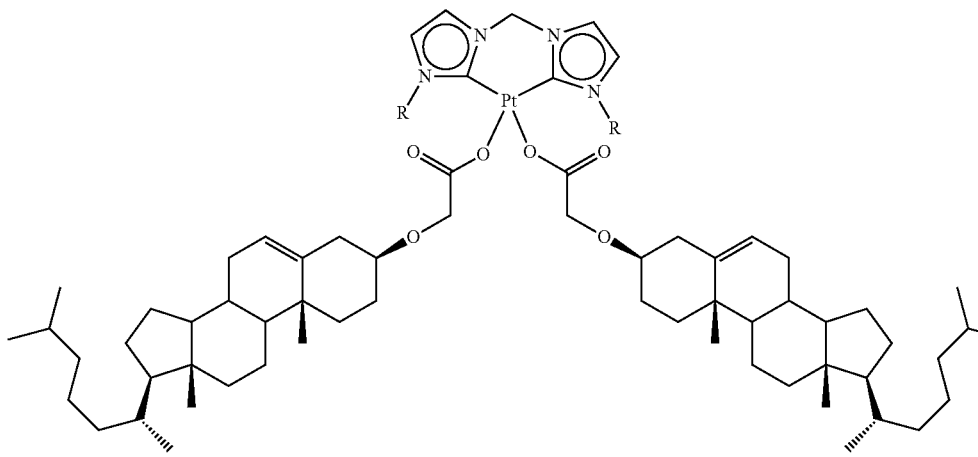

and

Compound 87

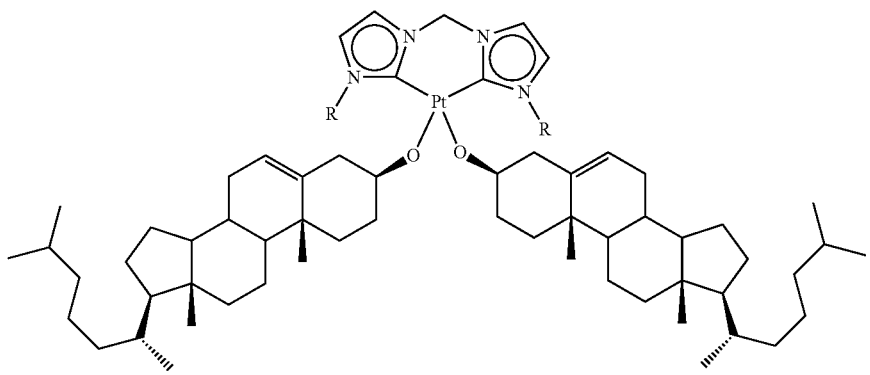

wherein, R is alkyl or substituted alkyl group(s). Further, alkyl is selected from a group comprising methyl, ethyl, propyl, i-propyl and butyl. Additionally, the substituted alkyl is $(CH2)_3—SO_3$.

In some embodiments, Formula VI represents abnormal N-heterocyclic-carbene (NHC) platinum(II) complexes [Compounds 88-94]:

Compound 88(example1)

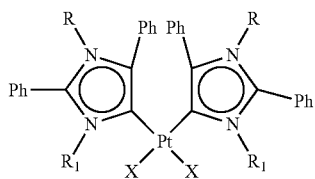

Compound 89

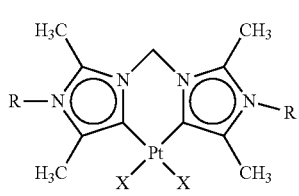

-continued

Compound 90 (example 3)

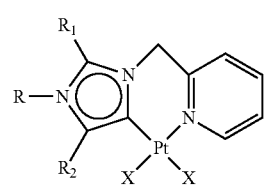

Compound 91(example 4)

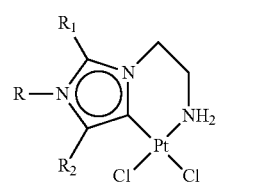

Compound 92(example 5)

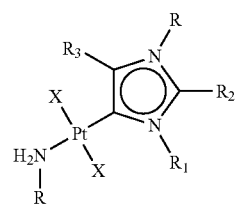

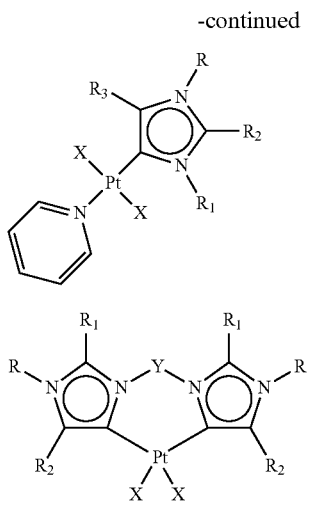

Compound 93 (example 6)

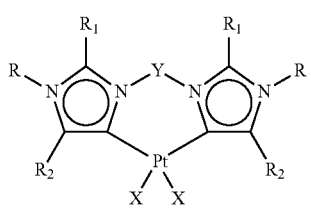

Compound 94(example 2)

wherein, 'R' is alkyl group(s) or substituted alkyl; 'X' is halide; and Y is selected from the group consisting of $CH_2$, $CH_2$—$CH_2$ and CO in Compounds 87-94. Further, alkyl is selected from a group comprising methyl, ethyl, propyl, i-propyl and butyl. Additionally, the substituted alkyl is $(CH2)_3$—$SO_3$ and 'halide' is further selected from chloride or iodide.

The present disclosure relates to the synthesis of a series of platinum based nanoparticles wherein, the diamminocyclohexyl-Pt (DACH-Pt) has a monocarboxylated covalent bond through a carboxylic acid and a co-ordination bond with amide oxygen. Dicarbonyl molecules (Dicarboxylic acids) such as succinic acid, malonic acid and oxalic acid are used which eventually form seven, six and five member rings with platinum (II) respectively. The linker between the platinum ring and cholesterol helps in forming linkages selected from a group comprising carbamate linkage, ether linkage or the likes or any combinations thereof. Therefore, some of the embodiments of the present disclosure relates to compounds represented by the general backbone: lipid-linker-dicarbonyl. These molecules are used to complex platinum compounds such as DACH-Pt, oxaliplatin, cisplatin, platinum containing carbenes or other platinates and platinum compounds, through covalent and/or coordination bonds.

In an embodiment of the present disclosure, several variants of platinum based compounds such as racemates, diastereomers and the likes are also provided.

In an embodiment of the present disclosure, any molecule that has two carbonyl groups may be used. In one embodiment, the dicarbonyl molecule is a dicarboxylic acid, such as, for example, succinic acid, malonic acid or oxalic acid.

The disclosure also provides particles comprising one or more of the platinum based compounds described herein, e.g., compounds of Formula (I), Formula (II), Formula (VI), or any combinations thereof. Generally, the particle disclosed herein can be of any shape or form, e.g., spherical, rod, elliptical, cylindrical, capsule, or disc; and these particles can be part of a network or an aggregate.

In some embodiments, the particle is a microparticle or a nanoparticle. As used herein, the term "microparticle" refers to a particle having a particle size of about 1 µm to about 1000 µm. As used herein, the term "nanoparticle" refers to particle having a particle size of about 0.1 nm to about 1000 nm. Generally, the particles have any size from nm to millimeters. In some embodiments, the particles can have a size ranging from about 5 nm to about 5000 nm. In some embodiments, the particles have an average diameter of from about 50 nm to about 2500 nm. In some embodiments, the particles have an average diameter of from about 100 nm to about 2000 nm. In some embodiments, the particles have an average diameter of from about 150 nm to about 1700 nm. In some embodiments, the particles have an average diameter of from about 200 nm to about 1500 nm. In some embodiment, the particles have an average diameter of about 260 nm. In one embodiment, the particles have an average diameter of about 30 nm to about 150 nm. In some embodiments, the particle have an average diameter of about 100 nm to about 1000 nm, from about 200 nm to about 800 nm, from about 200 nm to about 700 nm, or from about 300 nm to about 700 nm.

In some embodiments, the particle has an average size of about 50 to about 1000 nm. In a further embodiment, the nanoparticles of the present invention are in the range of about 50 to about 500 nm. In another embodiment, the nanoparticles of the present invention are in the range of about 50 to about 500 nm. In one embodiment, the particle has a size of about 500 nm.

It will be understood by one of ordinary skill in the art that particles usually exhibit a distribution of particle sizes around the indicated "size." Unless otherwise stated, the term "particle size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particles can be substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration.

What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

In addition to the platinum compounds disclosed herein, the particle can comprise co-lipids and/stabilizers. Additional lipids can be included in the particles for a variety of purposes, such as to prevent lipid oxidation, to stabilize the bilayer, to reduce aggregation during formation or to attach ligands onto the particle surface. Any of a number of additional lipids and/or other components can be present, including amphipathic, neutral, cationic, anionic lipids, and programmable fusion lipids. Such lipids and/or components can be used alone or in combination. One or more components of particle can comprise a ligand, e.g., a targeting ligand.

In some embodiments, the particle further comprises a phospholipid. Without limitations, the phospholipids can be of natural origin, such as egg yolk or soybean phospholipids, or synthetic or semisynthetic origin. The phospholipids can be partially purified or fractionated to comprise pure fractions or mixtures of phosphatidyl cholines, phosphatidyl cholines with defined acyl groups having 6 to 22 carbon atoms, phosphatidyl ethanolamines, phosphatidyl inositols, phosphatidic acids, phosphatidyl serines, sphingomyelin or phosphatidyl glycerols. Suitable phospholipids include, but are not limited to, phosphatidylcholine, phosphatidylglycerol, lecithin, β,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), 1-stearoyl-2-oleoyl phosphatidylcholine (SOPC), 1,2-distearoyl-sn-glycem-3-phosphoethanolamine (DSPE), and any combinations thereof. Non-phosphorus containing lipids can also be used. These include, e.g., stearylamine, docecylamine, acetyl palmitate, fatty acid amides, and the like. Other phosphorus-lacking compounds, such as sphingolipids, glycosphingolipid families, diacylglycerols, and β-acyloxyacids, can also be used In some embodiments, the phospholipid in the particle is selected from the group consisting of 1,2-Didecanoyl-sn-glycero-3-phosphocholine; 1,2-Dierucoyl-sn-glycero-3-phosphate (Sodium Salt); 1,2-Dierucoyl-sn-glycero-3-phosphocholine; 1,2-Dierucoyl-sn-glycero-3-phosphoethanolamine; 1,2-Dierucoyl-sn-glycero-3 [Phospho-rac-(1-glycerol) (Sodium Salt); 1,2-Dilinoleoyl-sn-glycero-3-phosphocholine; 1,2-Dilauroyl-sn-glycero-3-phosphate (Sodium Salt); 1,2-Dilauroyl-sn-glycero-3-phosphocholine; 1,2-Dilauroyl-sn-glycero-3-phosphoethanolamine; 1,2-Dilauroyl-sn-glycero-3 [Phospho-rac-(1-glycerol) (Sodium Salt); 1,2-Dilauroyl-sn-glycero-3[Phospho-rac-(1-glycerol) (Ammonium Salt); 1,2-Dilauroyl-sn-glycero-3-phosphoserine (Sodium Salt); 1,2-Dimyristoyl-sn-glycero-3-phosphate (Sodium Salt); 1,2-Dimyristoyl-sn-glycero-3-phosphocholine; 1,2-Dimyristoyl-sn-glycero-3-phosphoethanolamine; 1,2-Dimyristoyl-sn-glycero-3[Phospho-rac-(1-glycerol) (Sodium Salt); 1,2-Dimyristoyl-sn-glycero-3[Phospho-rac-(1-glycerol) (Ammonium Salt); 1,2-Dimyristoyl-sn-glycero-3[Phospho-rac-(1-glycerol) (Sodium/Ammonium Salt); 1,2-Dimyristoyl-sn-glycero-3-phosphoserine (Sodium Salt); 1,2-Dioleoyl-sn-glycero-3-phosphate (Sodium Salt); 1,2-Dioleoyl-sn-glycero-3-phosphocholine; 1,2-Dioleoyl-sn-glycero-3-phosphoethanolamine; 1,2-Dioleoyl-sn-glycero-3[Phospho-rac-(1-glycerol) (Sodium Salt); 1,2-Dioleoyl-sn-glycero-3-phosphoserine (Sodium Salt); 1,2-Dipalmitoyl-sn-glycero-3-phosphate (Sodium Salt); 1,2-Dipalmitoyl-sn-glycero-3-phosphocholine; 1,2-Dipalmitoyl-sn-glycero-3-phosphoethanolamine; 1,2-Dipalmitoyl-sn-glycero-3[Phospho-rac-(1-glycerol) (Sodium Salt); 1,2-Dipalmitoyl-sn-glycero-3[Phospho-rac-(1-glycerol) (Ammonium Salt); 1,2-Dipalmitoyl-sn-glycero-3-phosphoserine (Sodium Salt); 1,2-Distearoyl-sn-glycero-3-phosphate (Sodium Salt); 1,2-Distearoyl-sn-glycero-3-phosphocholine; 1,2-Distearoyl-sn-glycero-3-phosphoethanolamine; 1,2-Distearoyl-sn-glycero-3 [Phospho-rac-(1-glycerol) (Sodium Salt); 1,2-Distearoyl-sn-glycero-3[Phospho-rac-(1-glycerol) (Ammonium Salt); 1,2-Distearoyl-sn-glycero-3-phosphoserine (Sodium Salt); Egg-PC; Hydrogenated Egg PC; Hydrogenated Soy PC; 1-Myristoyl-sn-glycero-3-phosphocholine; 1-Palmitoyl-sn-glycero-3-phosphocholine; 1-Stearoyl-sn-glycero-3-phosphocholine; 1-Myristoyl-2-palmitoyl-sn-glycero 3-phosphocholine; 1-Myristoyl-2-stearoyl-sn-glycero-3-phosphocholine; 1-Palmitoyl-2-myristoyl-sn-glycero-3-phosphocholine; 1-Palmitoyl-2-oleoyl-sn-glycero-3-phosphocholine; 1-Palmitoyl-2-oleoyl-sn-glycero-3-phosphoethanolamine; 1-Palmitoyl-2-oleoyl-sn-glycero 3 [Phospho-rac-(1-glycerol)] (Sodium Salt); 1-Palmitoyl-2-stearoyl-sn-glycero-3-phosphocholine; 1-Stearoyl-2-myristoyl-sn-glycero-3-phosphocholine; 1-Stearoyl-2-oleoyl-sn-glycero-3-phosphocholine; and 1-Stearoyl-2-palmitoyl-sn-glycero-3-phosphocholine. In some embodiments, the phospholipid is SPOC, egg PC, or Hydrogenated Soy PC (HSPC). In one, the phospholipid in the composition is HSPC.

In some embodiments, the particle further comprises a polyethylene glycol (PEG). The PEG can be included in the particle by itself or conjugated with a component present in the particle. For example, the PEG can be conjugated with the platinum based compound or a co-lipid/stabilizer component of the particle. In some embodiments, the PEG is conjugated with a co-lipid component of the particle. Without limitations, the PEG can be conjugated with any co-lipid. For example, the PEG conjugated co-lipid can be selected from the group consisting of PEG conjugated diacylglycerols and dialkylglycerols, PEG-conjugated phosphatidylethanolamine, PEG conjugated to phosphatidic acid, PEG conjugated ceramides (see, U.S. Pat. No. 5,885,613), PEG conjugated dialkylamines, PEG conjugated 1,2-diacyloxypropan-3-amines, and PEG conjugated to 1,2-distearoyl-sn-glycem-3-phosphoethanolamine (DSPE), and any combinations thereof. In some embodiments, the PEG conjugated lipid is 1,2-distearoyl-sn-glycem-3-phosphoethanolamine-N-[amino(polyethylene glycol)-2000] (DSPE-PEG2000).

In some embodiments, the particle further comprises a surfactant. Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

In some embodiments, th particle can further comprise acationic lipid. Exemplary cationic lipids include, but are not limited to, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.C1), 1,2-Dilinoleoyl-3-trimethylaminopropane chloride salt (DLin-TAP.C1), 1,2-Dilinoleyloxy-3—(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3 aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis (2-hydroxydodecyl)amino)ethyl)(2-hydroxydodecyl)amino) ethyl)piperazin-1-yl)ethylazanediyl)didodecan-2-ol (Tech Gi), or a mixture thereof.

In some embodiments, the particle further comprises a non-cationic lipid. The non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), di stearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof.

The conjugated lipids that inhibit aggregation of particles can also be included in the particles disclosed herein. Such lipids include, but are not limited to, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles can be from 0.01 mol % to about 20 mol % or about 2 mol % of the total lipid present in the particle.

In some embodiments, the particle is in the form of a liposome, vesicle, or emulsion. As used herein, the term "liposome" encompasses any compartment enclosed by a lipid layer. Liposomes can have one or more lipid membranes. Liposomes can be characterized by membrane type and by size. Small unilamellar vesicles (SUVs) have a single membrane and typically range between 0.02 and 0.05 µm in diameter; large unilamellar vesicles (LUVS) are typically larger than 0.05 µm. Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

In order to form a liposome the lipid molecules comprise elongated non-polar (hydrophobic) portions and polar (hydrophilic) portions. The hydrophobic and hydrophilic portions of the molecule are preferably positioned at two ends of an elongated molecular structure. When such lipids are dispersed in water they spontaneously form bilayer membranes referred to as lamellae. The lamellae are composed of two mono layer sheets of lipid molecules with their non-polar (hydrophobic) surfaces facing each other and their polar (hydrophilic) surfaces facing the aqueous medium. The membranes formed by the lipids enclose a portion of the aqueous phase in a manner similar to that of a cell membrane enclosing the contents of a cell. Thus, the bilayer of a liposome has similarities to a cell membrane without the protein components present in a cell membrane.

A liposome composition can be prepared by a variety of methods that are known in the art. See e.g., U.S. Pat. No. 4,235,871, U.S. Pat. No. 4,897,355 and U.S. Pat. No. 5,171,678; published PCT applications WO 96/14057 and WO 96/37194; Felgner, P. L. et al., *Proc. Natl. Acad. Sci.*, USA (1987) 8:7413-7417, Bangham, et al. M. *Mol. Biol.* (1965) 23:238, Olson, et al. *Biochim. Biophys. Acta* (1979) 557:9, Szoka, et al. *Proc. Natl. Acad. Sci.* (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol.* (1984) 115:757, content of all of which is incorporated herein by reference in its entirety.

The liposomes can be prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323, content of which is incorporated herein by reference in its entirety.

The particles can also be in the form of an emulsion. Emulsions are typically heterogenous systems of one liquid dispersed in another in the form of droplets (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the conjugate disclosed herein can be present as a solution in either the aqueous phase or the oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers can broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials can also be included in emulsion formulations and contribute to the properties of emulsions. These include, but are not limited to, fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The applications of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199).

Exemplary surfactants for inclusion in the particles disclosed herein include but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191, 105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs. Microemulsions have also been effective in the transdermal delivery of active components in both cosmetic and pharmaceutical applications. It is expected that the microemulsion compositions and formulations of the present invention will facilitate the increased systemic absorption of the platinum based compounds from the gastrointestinal tract, as well as improve the local cellular uptake of platinum based compounds disclosed herein.

The design and synthesis of oxaliplatin nanoparticle is based on their structure-activity relationship. The present disclosure describes the synthesis of various platinum based amphiphiles by functional group interchange chemistry. After the synthesis, the final platinum adducts are formulated into nanoparticles with different co-lipids selected from Soy-PC, DOPE, DOPC etc and stabilizers selected from DSPE-PEG-OMe etc. Further, the characterization of all intermediates are performed by $^1$HNMR and the characterization of the final oxaliplatin amphiphile molecule is carried out using $^1$HNMR and MALDI-TOF respectively.

In an embodiment, a Platinum (IV) containing carbenes [Compound 101 and Compound 102] are also provided by the present disclosure.

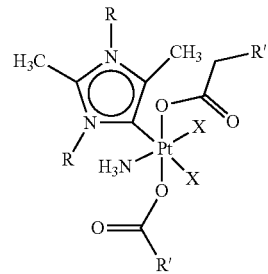

Compound 101

-continued

Compound 102

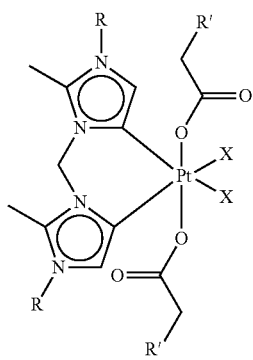

R = Me, Et, Pr, iPr, Bu, (CH$_2$)$_3$SO$_3$
R' = alkyl group or lipid (with or without linker)
X = Cl, I In another embodiment as described above, the platinum compound employed in the synthesis of platinum based amphiphiles in the present disclosure is selected from platinum containing carbenes. Preferably, said platinum containing carbenes are abnormal N-heterocyclic-carbene (NHC) platinum(II) complexes. Further, said abnormal NHC platinum(II) complexes are selected from, but not limited to Compounds 88, 90, 91, 92, 93 and 94.

In a further embodiment, the above mentioned NHC platinum(II) complexes are classified into the following classes:

(A) Two Abnormal Carbenes with 'Cis' Arrangement

Compound 88(example 1)

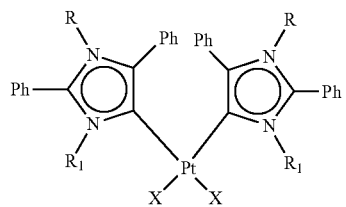

Compound 94(example 2)

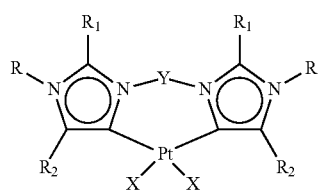

wherein R, R$_1$, R$_2$ are independently alkyl group or substituted alkyl group or phenyl or substituted phenyl; Y is (CH$_2$), (CH$_2$—CH$_2$) or (CO); and X is halide. In some embodiments, alkyl can be selected from the group comprising methyl, ethyl, propyl, i-propyl and butyl. In some embodiments, the substituted alkyl is (CH2)$_3$—SO$_3$. In some embodiments, halide is chloride or iodide.

(A) One Abnormal Carbene Donor: 'Cis' Arrangement with Respect to 'N' Donor Site Compound 90 (example 3)

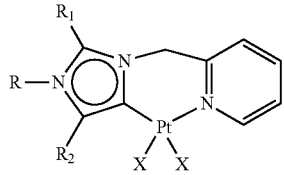

Compound 91(example 4)

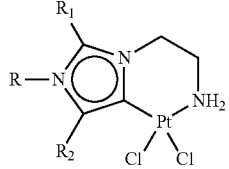

wherein R, R$_1$, R$_2$ are independently alkyl group or substituted alkyl or phenyl or substituted phenyl; Y is (CH$_2$), (CH$_2$—CH$_2$) or (CO); and X is halide. In some embodiments, alkyl can be selected from the group comprising methyl, ethyl, propyl, i-propyl and butyl. In some embodiments, the substituted alkyl is (CH2)$_3$—SO$_3$. In some embodiments, halide is chloride or iodide.

(B) One Abnormal Carbene Donor: 'Trans' Arrangement with Respect to 'N' Donor Site Compound 92(example 5)

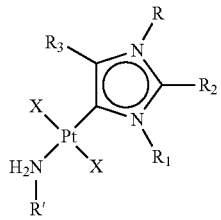

Compound 93 (example 6)

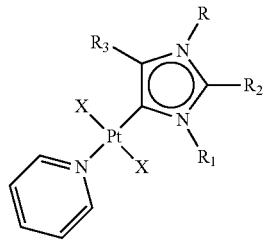

wherein R, R$_1$, R$_2$, R$_3$ are independently alkyl group or substituted alkyl or phenyl or substituted phenyl; Y is (CH$_2$), (CH$_2$—CH$_2$) or (CO); and X is halide. In some embodiments, alkyl can be selected from the group comprising methyl, ethyl, propyl, i-propyl and butyl. In some embodiments, the substituted alkyl is (CH2)$_3$—SO$_3$. In some embodiments, halide is chloride or iodide.

Some exemplary NHC platinum(II) complexes of Example 1 belonging to Compound 88 (two abnormal carbene ligands (without bridge) bonded to platinum in 'cis' fashion) are as follows:

Compounds 1A, 1B, 1C, 1D, 1E, 1F, 1G, 1G', 1H, 1H' and 1H"
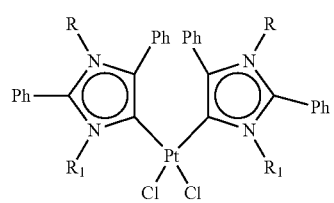
1A
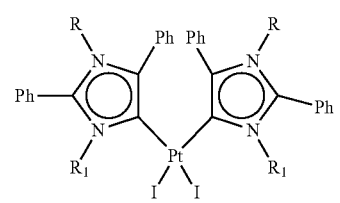
1B
R, R₁ = Me, Et, P, i-Pr, Ph, ——(CH₂)₃SO₃
R' = alkyl groups or lipid substitution
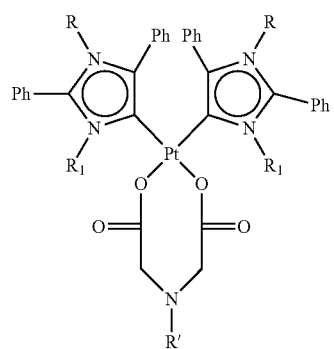
1C
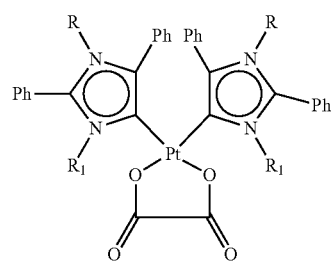
1D
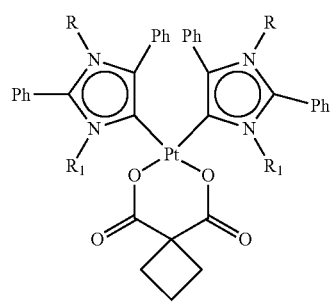
1E
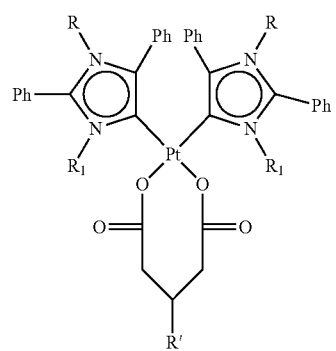
1F
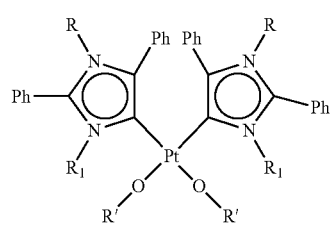
1G -continued
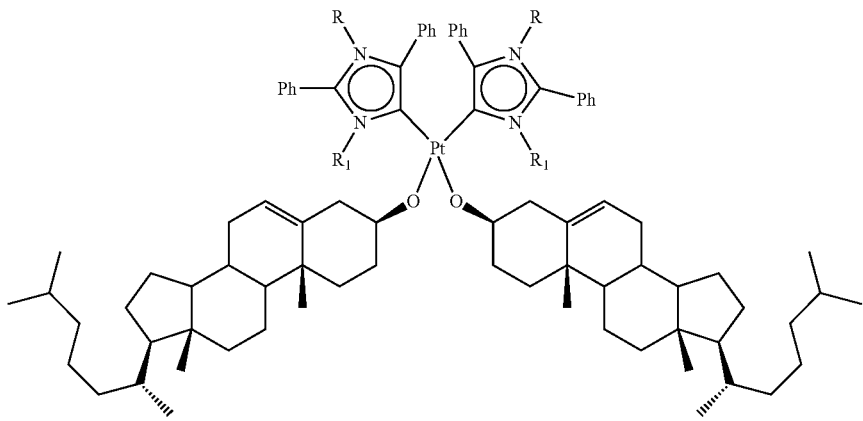
1G'
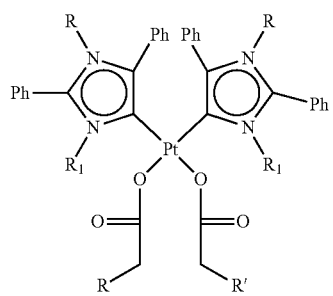
1H
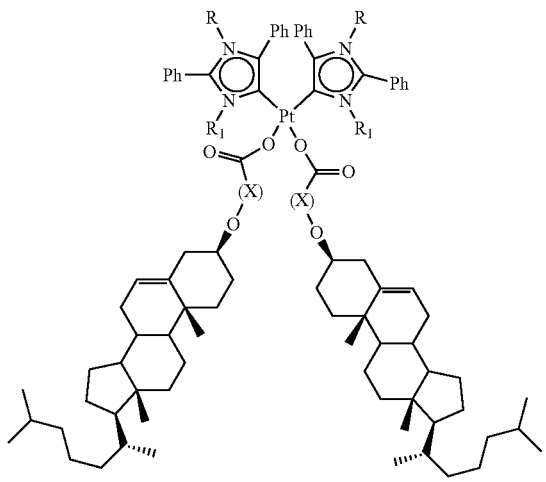
1H'
(cholesterol acid derivative complex)
X = linker
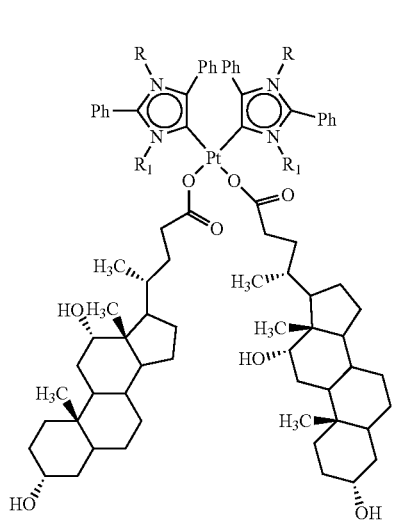
1H"

Some exemplary NHC platinum(II) complexes of Example 2 belonging to Compound 94 (one abnormal carbene ligand (with bridge and two donor center) are bonded to platinum in 'cis' fashion) are as follows:
Compounds 2A, 2B, 2C, 2D, 2E, 2F, 2G, 2G', 2H, 2H' and 2H''
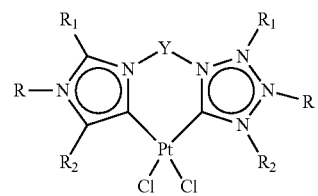
2A
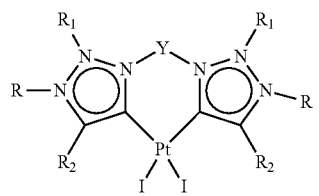
2B
R, $R_1$, $R_2$ = Me, Et, P, i-Pr, Ph, —(CH$_2$)$_2$SO$_3$
Y = CH$_2$; CH$_2$—CH$_2$; CO
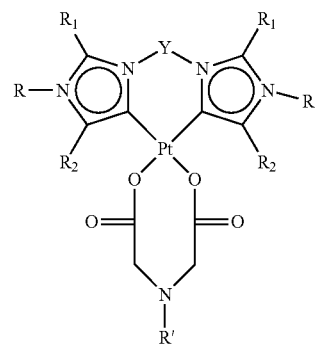
2C
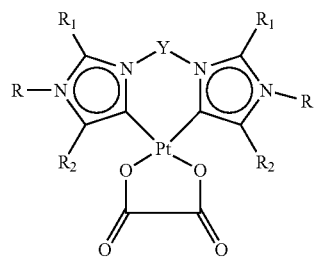
2D
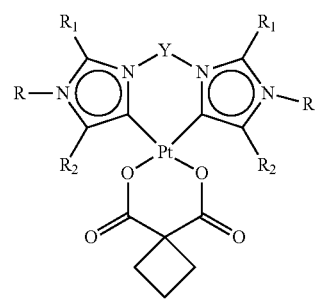
2E
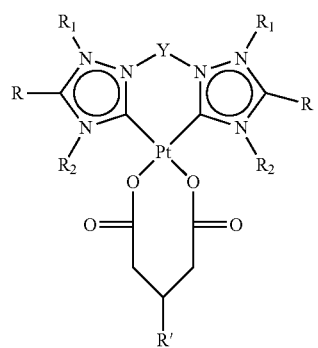
2F
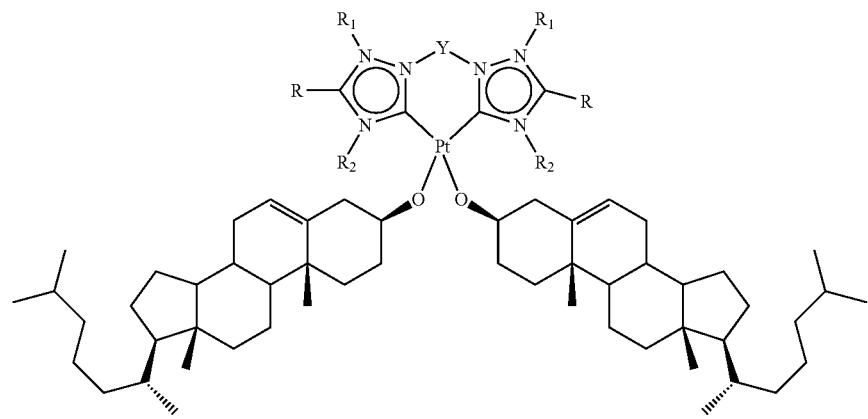

-continued
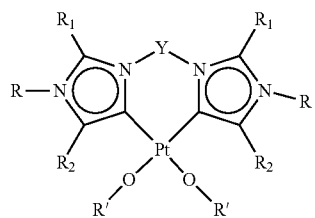
2G
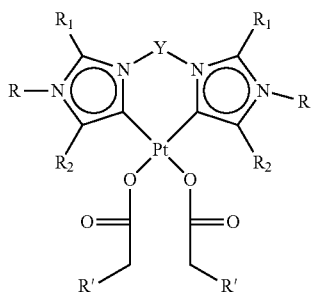
2H
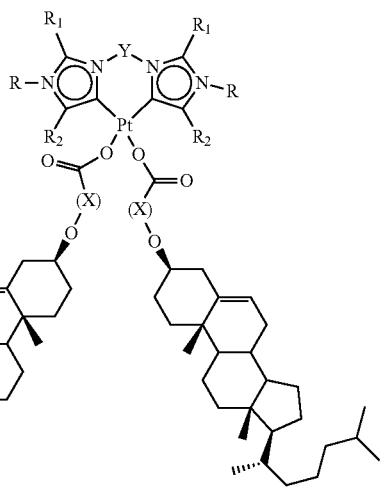
2H'
(cholesterol acid derivative complex)
X = linker
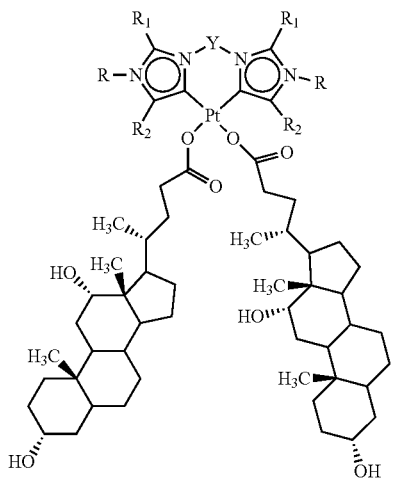
2H"
Some exemplary NHC platinum(II) complexes of Example 3 belonging to Compound 90 (one abnormal carbene donor bridged with pyridine donor, are bonded to platinum in 'cis' fashion) are as follows:
Compounds 3A, 3B, 3C, 3D, 3E, 3F, 3G, 3G', 3H, 3H' and 3H"
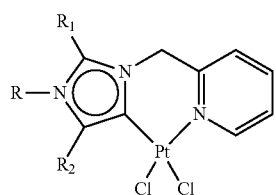
3A
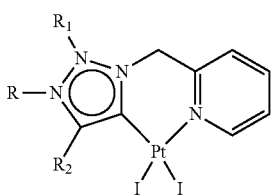
3B
R, R1, R2 = Me, Et, Pr, i-Pr, Ph, ——(CH$_2$)$_3$SO$_3$
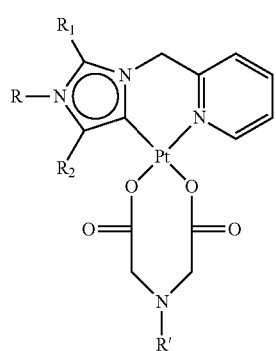
3C
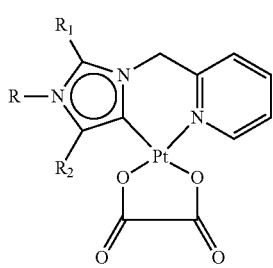
3D -continued
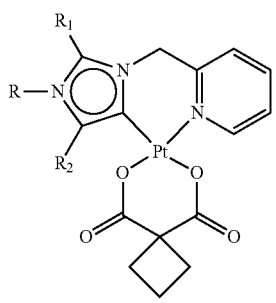
3E
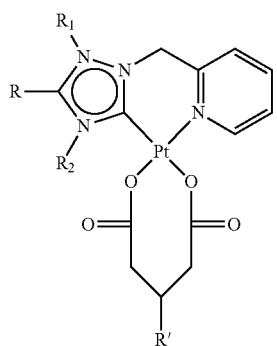
3F
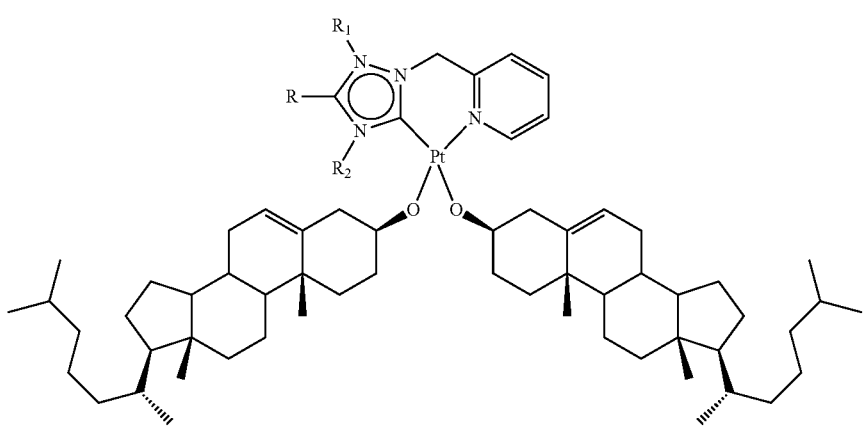
3G'
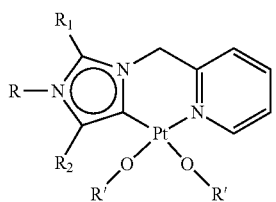
3G
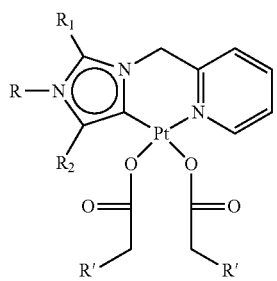
3H
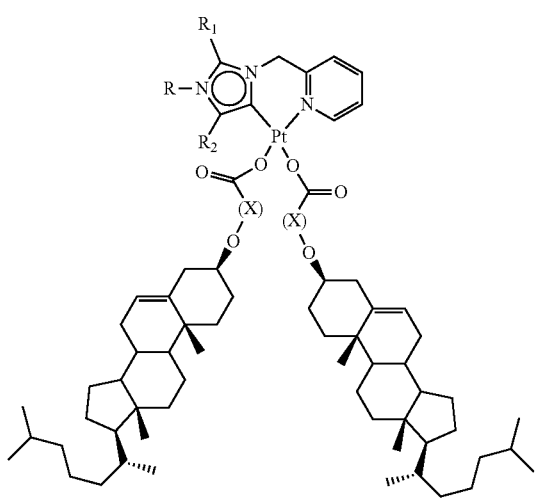
(cholesterol acid derivative complex)
X = linker
3H'
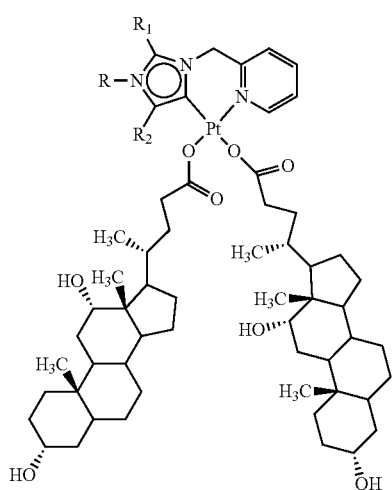
3H'

Some exemplary NHC platinum(II) complexes of Example 4 belonging to Compound 91 (one abnormal carbene donor bridged with primary amine donor, are bonded to platinum in 'cis' fashion) are as follows:
Compounds 4A, 4B, 4C, 4D, 4E, 4F, 4G, 4G', 4H, 4H' and 4H''
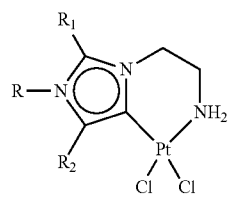
4A
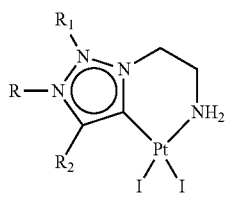
4B
R, R1, R2 = Me, Et, Pr, i-Pr, Ph, —(CH$_2$)$_3$SO$_3$
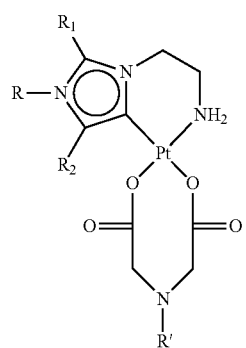
4C
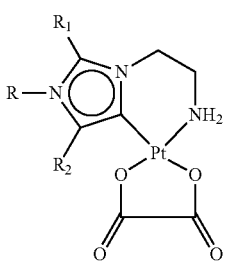
4D
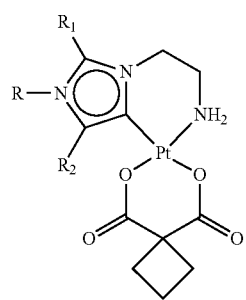
4E
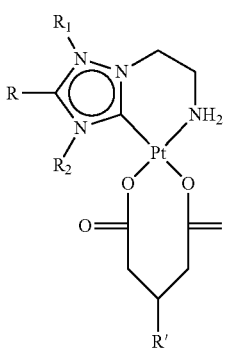
4F
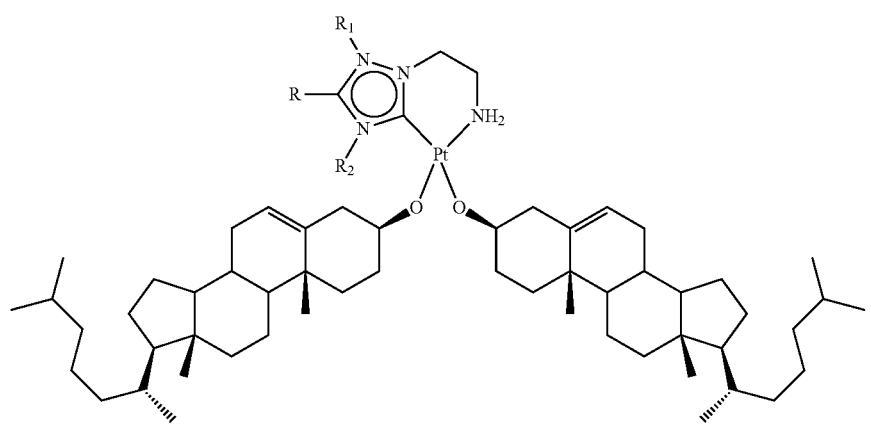
4G'

-continued
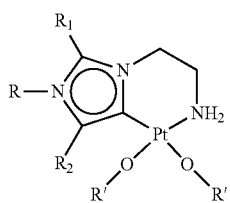
3G
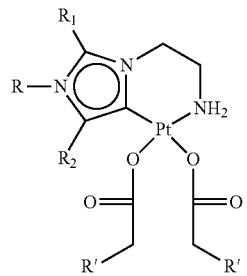
4H
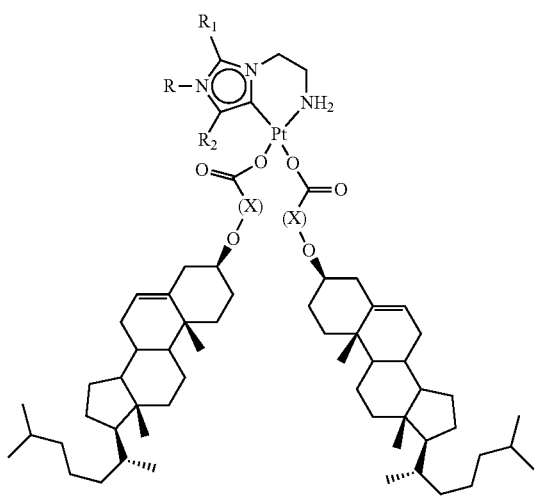
4H'
(cholesterol acid derivative complex)
X = linker
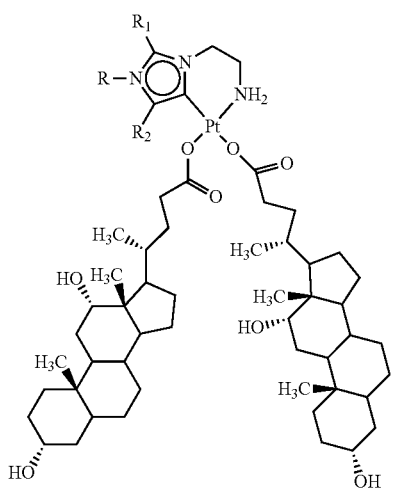
4H"
Some exemplary NHC platinum(II) complexes of Example 5 belonging to Compound 92 (one abnormal carbene donor and one primary amine donor, are bonded to platinum in 'trans' fashion) are as follows:
Compounds 5A, 5B, 5C, 5C', 5D, 5D' and 5D"
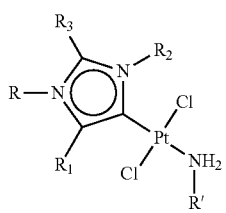
5A
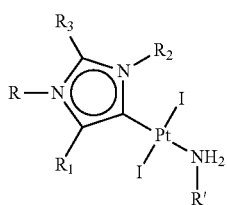
5B
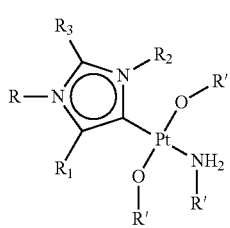
5C -continued
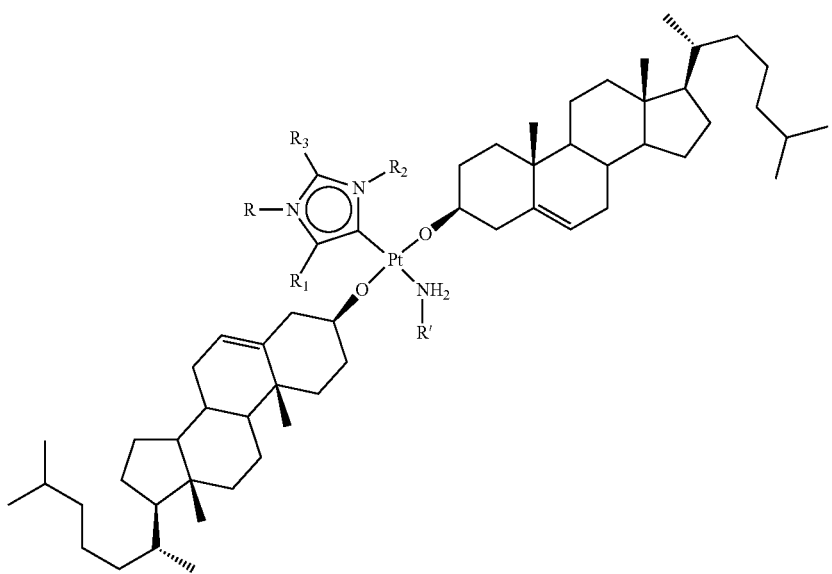
5C'
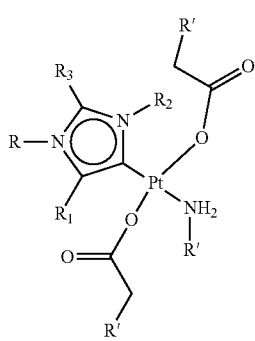
5D
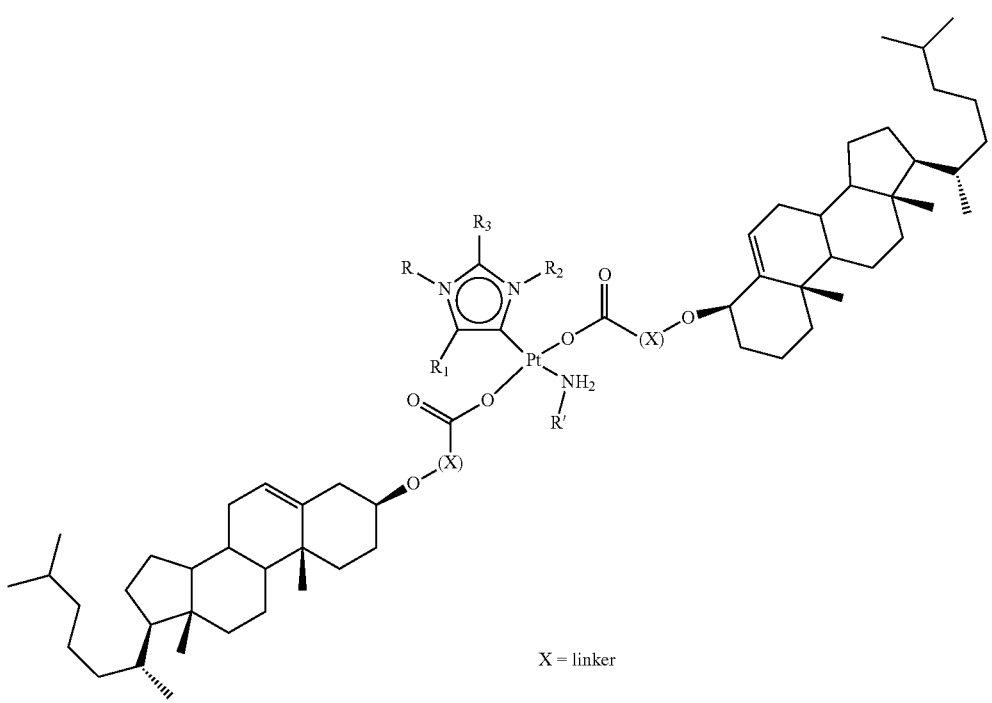
5D'
X = linker -continued
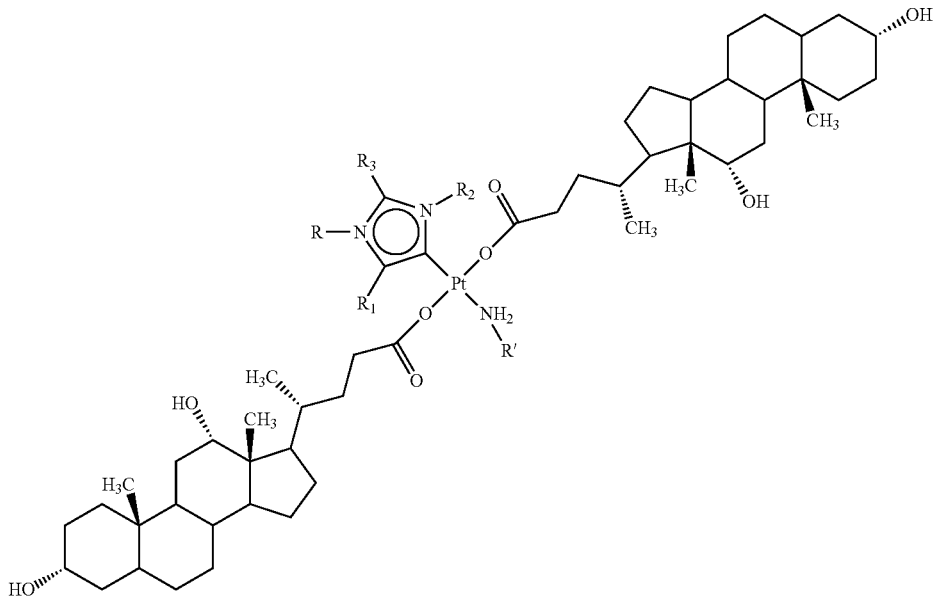
5D″
R, R₁, R₂, R₃, = Me, Et, Pr, i-Pr, Ph, —(CH₂)₃SO₃
R′ = Et, Pr, i-Pr
Some exemplary NHC platinum(II) complexes of Example 6 belonging to Compound 93 (one abnormal carbene donor and one pyridine donor, are bonded to platinum in 'trans' fashion) are as follows:
Compounds 6A, 6B, C, 6C', 6D, 6D' and 6D″
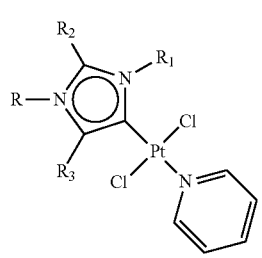
6A
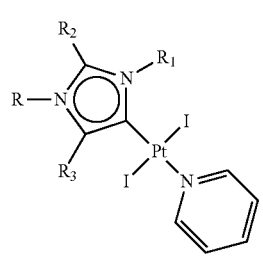
6B
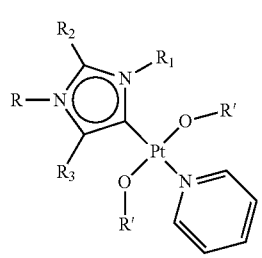
6C -continued
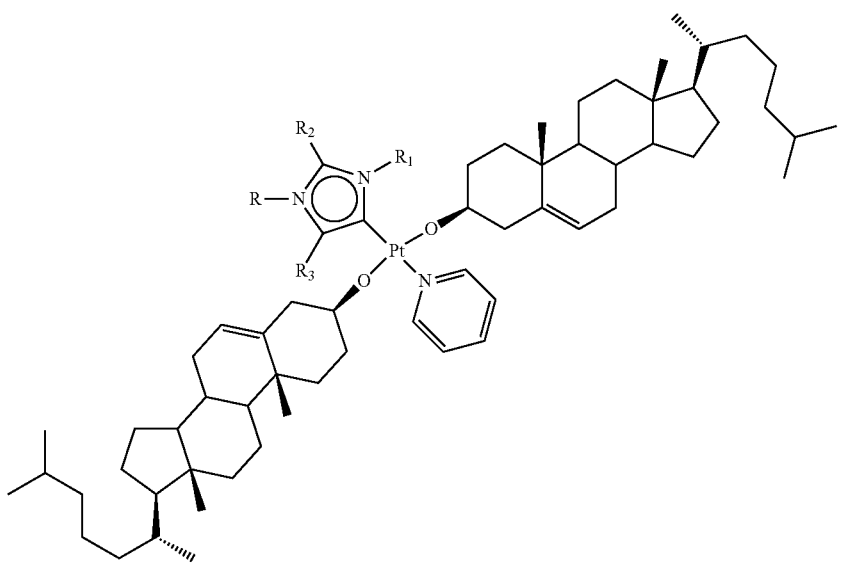
6C'
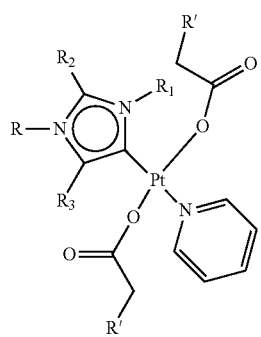
6D
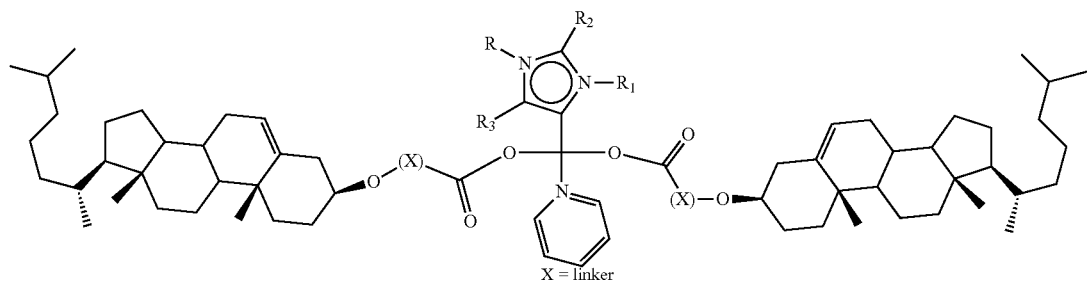
6D'
(cholesterol acid derivative complex)
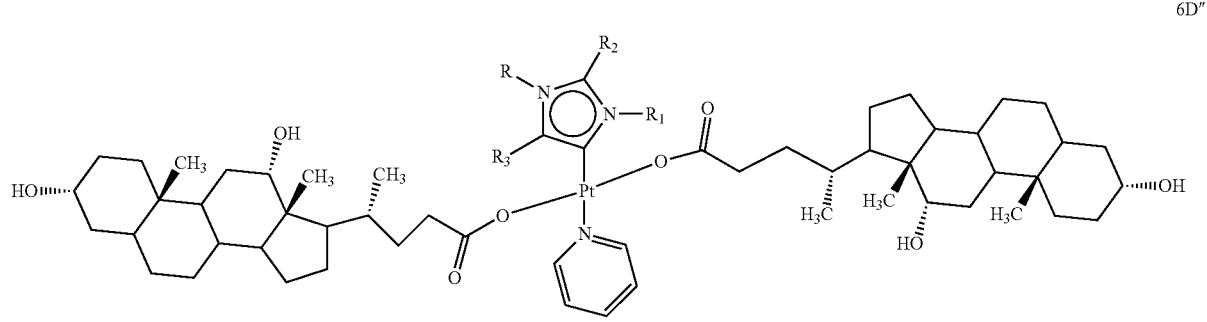
6D"
(deoxycholic acid complex)
R, R₁, R₂, R₃, = Me, Et, i-Pr, Ph, —(CH₂)₂SO₃

Without wishing to be bound by a theory, the nanoparticle compositions of the present disclosure show significant cancer cell killing efficacy. Exemplary nanoparticles were tested in different cancer cell lines and it was observed that the compounds demonstrated significantly better cell killing efficacy than the control compounds such as conventionally known platinum drugs oxaliplatin, cisplatin, oxaliplatin, carboplatin, paraplatin and sartraplatin.

Accordingly, in antoher aspect, described herein is a method of treating cancer, Generally, the method comprises administering a therapeutically effective amount of a platinum based compounds disclosed herein to a subject in need thereof.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Determination of a therapeutically effective amount is well within the capability of those skilled in the art. Generally, a therapeutically effective amount can vary with the subject's history, age, condition, sex, as well as the severity and type of the medical condition in the subject, and administration of other agents alleviate the disease or disorder to be treated.

Usually the amount of active compounds is between 0.1-95% by weight of the preparation, preferably between 0.2-20% by weight in preparations for parenteral use and preferably between 1 and 50% by weight in preparations for oral administration.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred. As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized.

The therapeutically effective dose can be estimated initially from cell culture assays. A dose can be formulated in animal models to achieve a circulating plasma concentration range that includes the IC50 (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay.

The dosage can be determined by a physician and adjusted, as necessary, to suit observed effects of the treatment. Generally, the compositions are administered so that the agent is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 tmg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that the agent has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In some embodiments, the platinum based compound can be administrated to a subject in combination with a pharmaceutically active agent, e.g., a second therapeutic agent. Exemplary pharmaceutically active compound include, but are not limited to, those found in *Harrison's Principles of Internal Medicine,* 13$^{th}$ Edition, Eds. T. R. Harrison et al. McGraw-Hill N.Y., NY; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; and United States Pharmacopeia, The National Formulary, USP XII NF XVII, 1990, the complete contents of all of which are incorporated herein by reference. The platinum based compound and the the second therapeutic agent can be administrated to the subject in the same pharmaceutical composition or in different pharmaceutical compositions (at the same time or at different times).

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrastemal injection and infusion. In some embodiments, the compositions are administered by intravenous infusion or injection.

As used herein, the term "cancer" refers to an uncontrolled growth of cells that may interfere with the normal functioning of the bodily organs and systems. Cancers that migrate from their original location and seed vital organs can eventually lead to the death of the subject through the functional deterioration of the affected organs. Metastasis is a cancer cell or group of cancer cells, distinct from the primary tumor location resulting from the dissemination of cancer cells from the primary tumor to other parts of the body. At the time of diagnosis of the primary tumor mass, the subject may be monitored for the presence of in transit metastases, e.g., cancer cells in the process of dissemination. As used herein, the term cancer, includes, but is not limited to the following types of cancer, breast cancer, biliary tract cancer, bladder cancer, brain cancer including Glioblastomas and medulloblastomas; cervical cancer; choriocarcinoma; colon cancer; endometrial cancer; esophageal cancer, gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma, Wilms tumor. Examples of cancer include but are not limited to, carcinoma, including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, Glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. Other cancers will be known to the artisan.

As used herein, the term "cancer" includes, but is not limited to, solid tumors and blood born tumors. The term cancer refers to disease of skin, tissues, organs, bone, cartilage, blood and vessels. The term "cancer" further encompasses primary and metastatic cancers. Examples of cancers that can be treated with the compounds of the invention include, but are not limited to, carcinoma, including that of the bladder, breast, colon, kidney, lung, ovary, pancreas, stomach, cervix, thyroid, and skin, including squamous cell carcinoma; hematopoietic tumors of lymphoid lineage, including, but not limited to, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma; hematopoietic tumors of myeloid lineage including, but not limited to, acute and chronic myelogenous leukemias and promyelocytic leukemia; tumors of mesenchymal origin including, but not limited to, fibrosarcoma, rhabdomyosarcoma, and osteosarcoma; other tumors including melanoma, seminoma, tetratocarcinoma, neuroblastoma, and glioma; tumors of the central and peripheral nervous system including, but not limited to, astrocytoma, neuroblastoma, glioma, and schwannomas; and other tumors including, but not limited to, xenoderma, pigmentosum, keratoactanthoma, thyroid follicular cancer, and teratocarcinoma. The methods disclosed herein are useful for treating patients who have been previously treated for cancer, as well as those who have not previously been treated for cancer. Indeed, the methods and compositions of this invention can be used in first-line and second-line cancer treatments.

As used herein, the term "precancerous condition" has its ordinary meaning, i.e., an unregulated growth without metastasis, and includes various forms of hyperplasia and benign hypertrophy. Accordingly, a "precancerous condition" is a disease, syndrome, or finding that, if left untreated, can lead to cancer. It is a generalized state associated with a significantly increased risk of cancer. Premalignant lesion is a morphologically altered tissue in which cancer is more likely to occur than its apparently normal counterpart. Examples of pre-malignant conditions include, but are not limited to, oral leukoplakia, actinic keratosis (solar keratosis), Barrett's esophagus, atrophic gastritis, benign hyperplasia of the prostate, precancerous polyps of the colon or rectum, gastric epithelial dysplasia, adenomatous dysplasia, hereditary nonpolyposis colon cancer syndrome (HNPCC), Barrett's esophagus, bladder dysplasia, precancerous cervical conditions, and cervical dysplasia.

In some embodiments, the cancer is selected from the group consisting of: breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer.

In some embodiments, the methods described herein relate to treating a subject having or diagnosed as having cancer. Subjects having cancer can be identified by a physician using current methods of diagnosing cancer. Symptoms and/or complications of cancer which characterize these conditions and aid in diagnosis are well known in the art and include but are not limited to, growth of a tumor, impaired function of the organ or tissue harboring cancer cells, etc. Tests that may aid in a diagnosis of, e.g. cancer include, but are not limited to, tissue biopsies and histological examination. A family history of cancer, or exposure to risk factors for cancer (e.g. tobacco products, radiation, etc.) can also aid in determining if a subject is likely to have cancer or in making a diagnosis of cancer.

In some embodiments, the method further comprises co-administering one or more additional anti-cancer therapy to the patient. In some embodiments, the additional therapy is selected from the group consisting of surgery, chemotherapy, radiation therapy, thermotherapy, immunotherapy, hormone therapy, laser therapy, anti-angiogenic therapy, and any combinations thereof. In some embodiments, the additional therapy comprises administering an anti-cancer agent to the patient. In some embodiments, the method comprises co-administering the conjugate and an anti-cancer agent or chemotherapeutic agent to the subject. As used herein, the term "anti-cancer agent" is refers to any compound (including its analogs, derivatives, prodrugs and pharmaceutically salts) or composition which can be used to treat cancer. Anti-cancer compounds for use in the present invention include, but are not limited to, inhibitors of topoisomerase I and II, alkylating agents, microtubule inhibitors (e.g., taxol), and angiogenesis inhibitors. Exemplary anti-cancer compounds include, but are not limited to, paclitaxel (taxol); docetaxel; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; platinate; carmustine; carmustine with Polifeprosan Implant; celecoxib; chlorambucil; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof. In some embodiments, the anti-cancer agent is a paclitaxel-carbohydrate conjugate, e.g., a paclitaxel-glucose conjugate, as described in U.S. Pat. No. 6,218,367, content of which is herein incorporated by reference in its entirety.

The methods of the invention are especially useful in combination with anti-cancer treatments that involve administering a second drug that acts in a different phase of the cell cycle.

For administration to a subject, the platinum based compounds and/or particles comprising said platinum based compunds are provided in pharmaceutically acceptable compositions. Accordingly, the disclosure also provides pharmaceutical compositions comprising the platinum based compounds or particles as disclosed herein. These pharmaceutically acceptable compositions comprise a therapeutically-effective amount of one or more of the platinum based compounds or particles described herein, formulated together with one or more pharmaceutically acceptable carriers (additives) and/or diluents. The said pharmaceutical compositions of the present invention are specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, the compounds of the present disclosure can be implanted into a patient or injected using a drug delivery system.

As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zincstearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as com starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (S) excipients, such as cocoa butter and suppository waxes; (9) oils, such as peanut oil, cottonseed oil, safflower oil, sesame oil, olive oil, com oil and soybean oil; (10) glycols, such as propylene glycol; (11) polyols, such as glycerin, sorbitol, mannitol and polyethylene glycol (PEG); (12) esters, such as ethyl oleate and ethyllaurate; (13) agar; (14) buffering agents, such as magnesium hydroxide and aluminum hydroxide; (15) alginic acid; (16) pyrogen-free water; (17) isotonic saline; (IS) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the likes are used interchangeably herein.

In some embodiments, the pharmaceutical composition comprising a platinum based compound can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a composition as described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, a composition as described herein can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008, 719; 5,674,533; 5,059,595; 5,591,767; 5,120,548; 5,073, 543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g.," is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, "management" or "managing" refers to preventing a disease or disorder from occurring in a subject, decreasing the risk of death due to a disease or disorder, delaying the onset of a disease or disorder, inhibiting the progression of a disease or disorder, partial or complete cure of a disease or disorder and/or adverse effect attributable to the said disease or disorder, obtaining a desired pharmacologic and/or physiologic effect (the effect may be prophylactic in terms of completely or partially preventing a disorder or disease or condition, or a symptom thereof and/or may be therapeutic in terms of a partial or complete cure for a disease or disorder and/or adverse effect attributable to the disease or disorder), relieving a disease or disorder (i.e. causing regression of the disease or disorder). Further, the present disclosure also envisages treating the said disease by administering the therapeutic composition of the instant disclosure.

The terms "subject" and "individual" are used interchangeably herein, and mean a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of cancer. In addition, the methods described herein can be used to treat domesticated animals and/or pets. A subject can be male or female. A subject can be one who has been previously diagnosed with or identified as suffering from cancer, but need not have already undergone treatment.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Synthesis of Platinum Containing Carbenes

Example 1: (A) Synthesis of Abnormal N-heterocyclic-carbene (NHC) Platinum(II) Complexes [Compounds 88, 90, 91, 92, 93 and 94]

(i) Synthesis of Abnormal NHC Platinum(II) Complexes Belonging to Compound 88 [Compounds 1A, 1B, 1C, 1D, 1E, 1F, 1G, 1G', 1H, 1H' and 1H" Respectively]

Scheme 1 Synthesis of dihalides of Example 1

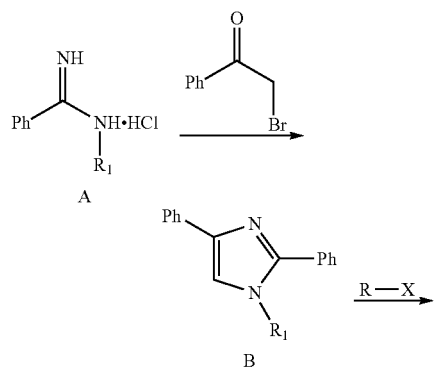

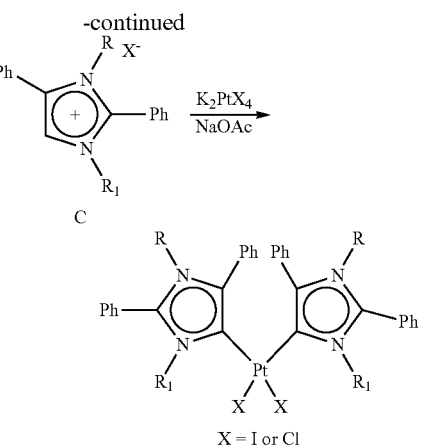

X = I or Cl

Synthesis of Compound B:

About 0.001 mole of 'A', phenacyl bromide (about 0.001) and potassium carbonate (about 0.0013 mole) are stirred at a temperature of about 20° C. for about two days in chloroform (about 3 ml) water (about 0.5 ml) mixture. The reaction is quenched with about 50 ml water and extracted by dichloromethane. Column chromatography is thereafter performed over silica gel with about 5% methanol chloroform mixture.

Synthesis of Compound C:

About 0.001 mole of 'B' and large excess of alkyl iodide/alkyl chloride/propane sultone is mixed and refluxed in acetonitrile for about 12 hours. Compound C is obtained as precipitate.

Characterization of C where R=propyl, $R_1$=phenyl, X=iodide:

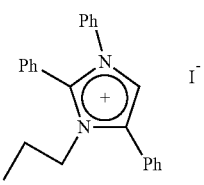

Characterization: $^1$H NMR (400 MHz)(CDCl$_3$): 0.61 (t), 1.47 (m), 4.14 (t), 7.38-7.56 (m), 7.85 (s), 7.87 (s); $^{13}$C NMR (400 MHz)(CDCl$_3$): 10.9, 22.9, 49.2, 121.3, 121.7, 125.2, 126.5, 129.3, 129.5, 129.8, 130.3, 130.6, 130.8, 131.4, 132.3, 134.7, 135.2; MALDI-TOF MS: $C_{24}H_{23}N_2$ (m/z)= 339.2 (M)$^+$; Mp. 88° C.

Characterization of C where R=—(CH$_2$)$_3$SO$_3$, $R_1$=phenyl, X=iodide:

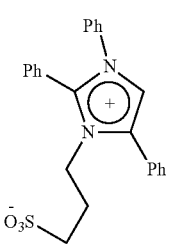

Characterization: $^1$H NMR (400 MHz)(dmso-d6): 1.74 (m), 2.12 (m), 4.22 (m), 7.48-7.74 (m), 8.37 (s); $^{13}$C NMR:

25.37, 48.18, 49.15, 122.01, 122.12, 125.85, 126.37, 129.17, 129.41, 129.53, 129.59, 130.10, 130.38, 131.02, 131.2, 132.16, 133.71, 135.02, 144.75: MALDI-TOF MS: $C_{24}H_{22}N_2O_3S$ (m/z)=418.1 (M); Mp. 297° C.

Synthesis of Compounds 1A/1B:

About 0.001 mole of chloride/iodide salt (C), potassium chloroplatinate/iodoplatinate (about 0.001 mole) and sodium acetate (about 0.002 moles) are mixed in DMSO and heated at about 120° C. for about 6 hours. The reaction mixture is allowed to come down to room temperature. Dichloromethane (about 50 ml) is added to the reaction mixture and the desired compound is separated as precipitate. The precipitate is washed by dichloromethane to get the pure Compounds 1A/1B.

Synthesis of Compound 1C (R'=H):

bout 0.001 moles of chloride complex (Compound 1A) and $AgBF_4$ (about 0.002 moles) in about 5 ml DMSO/DCM (1:1) mixture are stirred for about 12 hours at room temperature. The obtained mixture is filtered through celite, DCM is evaporated and barium salt of iminodiacetic acid (about 0.001 moles) in about 5 ml water is added and stirred at room temperature for about 24 hours. Compound 1C separates out as a precipitate and the same is filtered and washed with diethyl ether to get the pure Compound 1C.

R' of Compound 1C can be any substituted or non-substituted aromatic, aliphatic moiety or lipids and Compound 1C with said substitutions are synthesized by following the similar procedure as mentioned above.

Synthesis of Compound 1D:

About 0.001 mole of chloride complex (Compound 1A), and $AgBF_4$ (0.002 moles) in 5 ml DMSO,DCM (1:1) mixture are stirred for about 12 hrs at room temperature. The mixture is filtered through celite, DCM is evaporated and sodium salt of oxalic acid in about 5 ml water is added and stirred at room temperature for about 24 hours. Compound 1D separates out as a precipitate which is filtered and washed with diethyl ether to get the pure Compound 1D.

Thesis of Compound 1E:

About 0.001 mole of chloride complex (Compound 1A) and $AgBF_4$ (about 0.002 moles) in about 5 ml DMSO/DCM (1:1) mixture are stirred for about 12 hours at room temperature. The obtained mixture is filtered through celite, DCM is evaporated and sodium salt of cyclobutane dicarboxylic acid in about 5 ml water is added and stirred at room temperature for about 24 hours. Compound 1E separates out as a precipitate which is filtered and washed with diethyl ether to get the pure Compound 1E.

Synthesis of Compound 1F (R'=Me):

This is prepared by employing similar procedure as followed for the synthesis of Compound 1E. Further, R' can be any substituted or non substituted aromatic, aliphatic moiety or lipids.

Synthesis of Compound 1G':

About 0.001 mole of cholesterol is treated with about 0.0012 mole of sodium hydride in THF and stirred at RT for about 12 hours. The solvent is evaporated and DMSO (about 1 ml) solution of residue is added to the DMSO (about 5 ml) solution of about 0.001 mole of Compound 1A. The mixture is stirred for about 24 hours at about 100° C. DCM is thereafter added to the reaction mixture to get the precipitate of Compound 1G'.

Synthesis of Compound 1G:

To obtain Compound 1G, any lipids or primary/secondary alcohols which contain a hydroxyl group (in the form of HO—R') are linked with abnormal carbene through platinum by following the above procedure as described for Compound 1G'.

Synthesis of Compound 1H':

About 0.001 mole of chloride complex (Compound 1A) and $AgBF_4$ (about 0.002 mole) in about 5 ml DMSO/DCM (1:1) mixture are stirred for about 12 hours at room temperature. The mixture is filtered through celite; DCM is evaporated and lithium salt of cholesterol acid (prepared by the reaction of cholesterol with ethyl bromo acetate and then hydrolysis of the ester group by lithium hydroxide) (about 0.002 mole) in about 5 ml water is added and stirred at room temperature for about 24 hours. Compound 1H' separates out as precipitate; which is filtered and washed with diethyl ether to get the pure Compound 1H'.

Synthesis of Compound 1H":

Similar procedure as mentioned above in the synthesis of Compound 1H' is followed for the preparation of 1H". About 0.002 moles of cholic acid or deoxycholic acid is used instead of cholesterol acid derivative.

Synthesis of Compound 1H:

To obtain Compound 1H, any lipid which contain a hydroxyl group, is converted to acid (in the form of COOH—$CH_2R'$) and is linked with abnormal carbene through platinum by following the above procedure as described for the synthesis of Compound 1H'.

Example 2: (ii) Synthesis of Abnormal NHC Platinum(II) Complexes Belonging to Compound 94 [Compounds 2A, 2B, 2C, 2D, 2E, 2F, 2G, 2G', 2H, 2H' and 2H" Respectively]

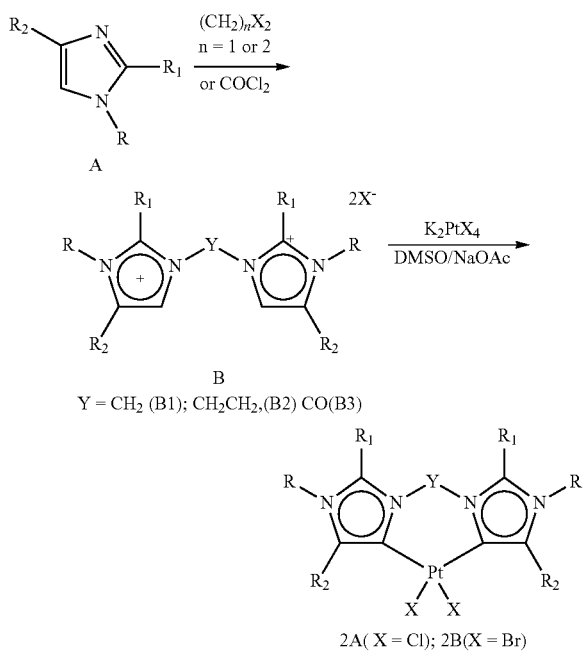

Synthesis of Compound B2:

About 0.01 moles of 'A' and diiodoethane or dichloroethane (about 0.005 moles) are stirred at about 140° C. in a high pressure vessel for about 12 hours. DMSO (about 20 ml) followed by dichloromethane (about 60 ml) is added to yield precipitate which is filtered and recrystallized in DMSO/DCM to get the pure Compound B2.

Further, Compound B1 is prepared in the same way as Compound B2.

Synthesis of Compound B3:

About 0.01 moles of 'A' and $COCl_2$ (excess; about 15% in toluene) are refluxed in a high pressure vessel for about 12 hours. Solvent is evaporated to get the pure compound B3 and the same is further use.

Synthesis of Compounds 2A/2B:

About 0.01 moles of salt (B), potassium chloroplatinate (about 0.01 moles) or potassium iodoplatinate (about 0.01 moles) and sodium acetate (0.02 moles) are mixed in DMSO and heated at about 120° C. for about 6 hours. The reaction mixture is allowed to come down to room temperature. Dichloromethane (about 50 ml) is added to the reaction mixture and the desired compound is separated as precipitate. The precipitate is washed by dichloromethane to get the pure Compounds 2A/2B.

Synthesis of Compound 2C (R=H):

About 0.01 moles of chloride complex (Compound 2A) and $AgBF_4$ (about 0.02 moles) in about 15 ml DMSO/DCM (1:1) mixture are stirred for about 16 hours at room temperature. The mixture is filtered through celite; DCM is evaporated and barium salt of iminodiacetic acid (0.01 moles) in about 5 ml water is added and stirred at room temperature for about 24 hours. Compound 2C separates out as a precipitate which is thereafter filtered and washed with diethyl ether to get the pure Compound 2C.

R' in Compound 2C is selected from any substituted or non substituted aromatic, aliphatic moiety or lipids and the Compounds with such substitutions are synthesized by following similar procedure as described for 2C.

Synthesis of Compound 2D:

About 0.001 moles of chloride complex (Compound 2A) and $AgBF_4$ (about 0.002 moles) in about 5 ml DMSO/DCM (1:1) mixture are stirred for about 12 hours at room temperature. The mixture is filtered through celite, DCM is evaporated and sodium salt of oxalic acid in about 5 ml water is added and stirred at room temperature for about 24 hrs. Compound 1C separates out as a precipitate which is filtered and washed with diethyl ether to get the pure Compound 2D.

Synthesis of Compound 2E:

About 0.001 mole of chloride complex (Compound 2A) and $AgBF_4$ (0.002 moles) in about 5 ml DMSO/DCM (1:1) mixture are stirred for about 12 hours at room temperature. The mixture id filtered through celite, DCM is evaporated and sodium salt of cyclobutane dicarboxylic acid in about 5 ml water is added and stirred at room temperature for about 24 hours. Compound 2E separates out as a precipitate which is filtered and washed with diethyl ether to get the pure Compound 2E.

Synthesis of Compound 2F (R=Me):

It is prepared by the similar procedure as followed for the synthesis of Compound 2E. R' is selected from any substituted or non substituted aromatic, aliphatic moiety or lipids.

Synthesis of Compound 2G':

About 0.001 moles of cholesterol is treated with about 0.0012 moles of sodium hydride in THF and stirred at RT for about 12 hours. The solvent is evaporated and DMSO (about 1 ml) solution of residue is added to the DMSO (about 5 ml) solution of about 0.001 moles of Compound 2A. The mixture is stirred for about 24 hours at about 100° C. DCM is added to the reaction mixture to obtain the precipitate of Compound 2G'.

Synthesis of Compound 2G:

Compound 2G is obtained by employing other lipids or primary/secondary alcohols which contain a hydroxyl group (in the form of HO-10 to link with abnormal carbene through platinum and by following the aforementioned procedure as described for the synthesis of Compound 2G'.

Synthesis of Compound 2H':

About 0.001 mole of chloride complex (Compound 2A) and $AgBF_4$ (about 0.002 mole) in about 5 ml DMSO/DCM (1:1) mixture are stirred for about 12 hours at room temperature. The resultant is filtered through celite; DCM is evaporated and lithium salt of cholesterol acid (prepared by the reaction of cholesterol with ethyl bromo acetate and then hydrolysis of the ester group by lithium hydroxide) (about 0.002 mole) in about 5 ml water is added and stirred at room temperature for about 24 hours.

Compound 2H' separates out as precipitate which is filtered and washed with diethyl ether to get the pure Compound 2H'.

Synthesis of Compound 2H":

Similar procedure is followed as described in the synthesis of Compound 2H'. However, about 0.002 moles of cholic acid or deoxycholic acid is used instead of cholesterol acid derivative.

Synthesis of 2H:

Compound 2H is obtained by employing any other lipid containing a hydroxyl group which can be converted to acid (in the form of $COOH$—$CH_2R'$). Said lipid is linked to abnormal carbene through platinum and the above procedure as described for the synthesis of Compound 2H' is followed.

Example 3: (iii) Synthesis of Abnormal NHC Platinum(H) Complexes Belonging to Compound 90 [Compounds 3A, 3B, 3C, 3D, 3E, 3F, 3G, 3G', 3H, 3H' and 3H" Respectively]

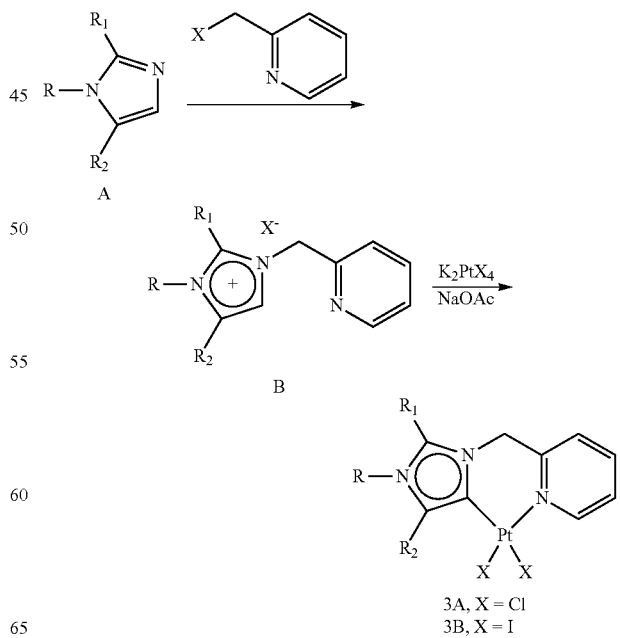

Synthesis of Compound B:

0.01 moles of 'A', hydrochloride salt of picolylchloride or picolyliodide (0.01 moles) and sodiumbicarbonate (0.012 moles) are taken in 10 ml ethanol and refluxed for about 24 hours. Solvent evaporated and the dichloromethane wash is given to extract compound B.

Compound B where $R_2$=H, R=Me, $R_1$=Me, X=I$^-$:

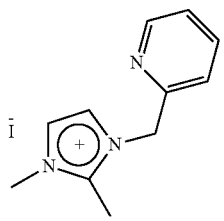

Characterization: $^1$H NMR (400 MHz)(dmso-d6): 2.60 (s), 3.81 (s), 5.61 (s), 7.36-7.39 (m), 7.51 (d), 7.71 (br, s), 7.76 (br, s), 7.86-7.89 (m), 8.52 (br, s). $^{13}$C NMR: 9.60, 34.86, 51.74, 121.84, 122.36, 122.43, 123.49, 137.48, 145.19, 149.56, 153.63. MALDI-TOF MS: $C_{11}H_{14}N_3$ (m/z)=188.12 (M)$^+$;

Synthesis of Compounds 3A/3B:

About 0.001 moles of chloride/iodide salt (B), potassium chloroplatinate (about 0.01 moles) or potassium iodoplatinate (about 0.001 moles) and sodium acetate (0.002 moles) are mixed in acetonitrile (about 10 ml) and the reaction mixture is refluxed for about 6 hours. The reaction mixture is allowed to come down to room temperature. The solvent is evaporated and the compounds 3A/3B are recrystallized from acetonitrile.

Synthesis of Compound 3C (R=H):

About 0.01 moles of chloride complex (Compound 3A) and AgBF$_4$ (about 0.02 moles) in about 15 ml DMSO/DCM (1:1) mixture are stirred for about 16 hours at room temperature. The mixture is filtered through celite; DCM is evaporated and barium salt of iminodiacetic acid (about 0.01 mole) in about 5 ml water is added and stirred at room temperature for about 24 hours. Compound 3C separates out as precipitate which is filtered and washed with diethyl ether to get the pure Compound 3C.

R' in Compound 3C is selected from any substituted or non substituted aromatic, aliphatic moiety or lipids and Compounds containing said substitutions are synthesized by following the procedure similar to as described in the synthesis of Compound 3C.

Synthesis of Compound 3D:

About 0.001 moles of chloride complex (Compound 3A) and AgBF$_4$ (about 0.002 mole) in about 5 ml DMSO/DCM (1:1) mixture are stirred for about 12 hours at room temperature. The mixture is filtered through celite; DCM is evaporated and sodium salt of oxalic acid in 5 ml water is added and stirred at room temperature for about 24 hours. Compound 3D separates out as precipitate which is thereafter filtered and washed with diethyl ether to get the pure Compound 3D.

Synthesis of Compound 3E:

About 0.001 moles of chloride complex (Compound 3A) and AgBF$_4$ (about 0.002 mole) in 5 ml DMSO/DCM (1:1) mixture are stirred for about 12 hours at room temperature. The mixture is filtered through celite, DCM is evaporated and sodium salt of cyclobutane dicarboxylic acid in about 5 ml water is added and stirred at room temperature for about 24 hours. Compound 3E separates out as precipitate which is thereafter filtered and washed with diethyl ether to get the pure Compound 3E.

Synthesis of Compound 3F (R=Me):

This is prepared by following the similar procedure as followed for the synthesis of Compound 3E. Further, R' in Compound 3F is selected from any substituted or non-substituted aromatic, aliphatic moiety or lipids.

Synthesis of Compounds 3G':

About 0.001 moles of cholesterol is treated with about 0.0012 mole of sodium hydride in THF and stirred at RT for about 12 hours. The solvent is evaporated and DMSO solution (about 1 ml) of residue is added to the DMSO (about 5 ml) solution of about 0.001 moles of Compound 3A. The mixture is stirred for about 24 hours at about 100° C. DCM is added to the reaction mixture to the precipitate of compound 3G' is obtained.

Synthesis of 3G:

Compound 3G is obtained by employing any other lipids or primary/secondary alcohols which contain a hydroxyl group (in the form of HO—R'). The said substituents are linked with abnormal carbene through platinum and compounds containing said substituents are obtained by following the above procedure as described for Compound 3G'.

Synthesis of 3H':

About 0.001 moles of chloride complex (Compound 3A) and AgBF$_4$ (about 0.002 moles) in about 5 ml DMSO/DCM (1:1) mixture are stirred for about 12 hours at room temperature. The mixture is filtered through celite; DCM is evaporated and lithium salt of cholesterol acid (prepared by the reaction of cholesterol with ethyl bromo acetate and then hydrolysis of the ester group by lithium hydroxide) (about 0.002 mole) in about 5 ml water is added and stirred at room temperature for about 24 hours. Compound 3H' separates out as precipitate which is filtered and washed with diethyl ether to get the pure Compound 3H'.

Synthesis of 3H'':

Similar procedure is followed as mentioned for the synthesis of 3H'. However, about 0.002 mole of cholic acid or deoxycholic acid is used instead of cholesterol acid derivative.

Synthesis of Compound 3H:

Compound 3H is prepared by employing any other lipid containing a hydroxyl group which is converted to acid (in the form of COOH—CH$_2$10 followed by linking the said lipid with abnormal carbene through platinum. Thereafter, the above procedure as described for the synthesis of compound 3H' is followed.

Example 4: (iv) Synthesis of Abnormal NHC Platinum(H) Complexes Belonging to Compound 91 [Compounds 4A, 4B, 4C, 4D, 4E, 4F, 4G, 4G', 4H, 4H' and 4H'' Respectively]

Scheme 4 Synthesis of dihalides of Example 4

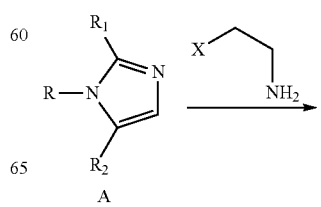

A

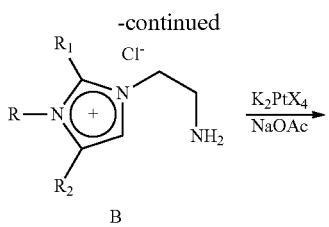

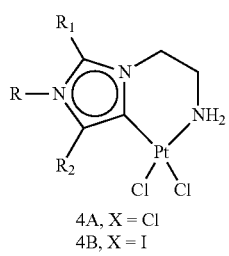

4A, X = Cl
4B, X = I

Synthesis of Compound B:

About 0.01 moles of 'A', 2-chloroethylamine or 2-iodoethylamine (about 0.01 moles) and potassium carbonate (about 0.01 moles) in about 5 ml of ethanol are stirred at about 25° C. for about 12 hours. The reaction mixture is filtered and diethyl ether is added to give a precipitate of compound B.

Synthesis of Compounds 4A/4B:

About 0.001 moles of chloride/iodide salt (B) potassium chloroplatinate (about 0.01 moles) or potassium iodoplatinate (about 0.001 moles) and sodium acetate (about 0.002 moles) are mixed in acetonitrile (about 10 ml) and refluxed for about 6 hours. The reaction mixture is allowed to come down to room temperature. The solvent is evaporated and the compound is recrystallized from acetonitrile.

Synthesis of Compound 4C (R=H):

About 0.01 moles of chloride complex (Compound 2A), and $AgBF_4$ (about 0.02 moles) in about 15 ml DMSO/DCM (1:1) mixture are stirred for about 16 hours at room temperature. The mixture is filtered through celite; DCM is evaporated and barium salt of iminodiacetic acid (about 0.01 moles) in about 5 ml water is added and stirred at room temperature for about 24 hours. The Compound 4C separates out as precipitate which is thereafter filtered and washed with diethyl ether to get the pure Compound 4C.

R' in Compound 4C is selected from any substituted or non-substituted aromatic, aliphatic moiety or lipids and compounds containing said substitutions are synthesized by following the similar procedure as described for Compound 4C.

Synthesis of Compound 4D:

About 0.001 moles of chloride complex (Compound 3A) and $AgBF_4$ (about 0.002 moles) in about 5 ml DMSO/DCM (1:1) mixture are stirred for about 12 hours at room temperature. The mixture is filtered through celite; DCM is evaporated and sodium salt of oxalic acid in about 5 ml water is added and stirred at room temperature for about 24 hours. The Compound 4D separates out as precipitate which is thereafter filtered and washed with diethyl ether to get the pure Compound 4D.

Synthesis of Compound 4E:

About 0.001 moles of chloride complex (Compound 4A) and $AgBF_4$ (about 0.002 mole) in about 5 ml DMSO/DCM (1:1) mixture are stirred for about 12 hours at room temperature. The mixture is filtered through celite, DCM is evaporated and sodium salt of cyclobutane dicarboxylic acid in about 5 ml water is added and stirred at room temperature for about 24 hours. The Compound 3E separates out as precipitate which is filtered and washed with diethyl ether to obtain the pure Compound 4E.

Synthesis of Compound 4F (R=Me):

This is prepared by following the similar procedure as described for the synthesis of Compound 4E. Further, R' in Compound 4F is selected from any substituted or non substituted aromatic, aliphatic moiety or lipids.

Synthesis of Compound 4G':

About 0.001 moles of cholesterol is treated with about 0.0012 moles of sodium hydride in THF and stirred at RT for about 12 hours. The solvent is evaporated and DMSO solution of residue (about 1 ml) is added to the DMSO (about 5 ml) solution of about 0.001 moles of Compound 4A. The mixture is stirred for about 24 hours at about 100° C. DCM is added to the reaction mixture to obtain the precipitate of compound 4G'.

Synthesis of Compound 4G:

Compound 4G is obtained by employing any other lipids or primary/secondary alcohols which contain a hydroxyl group (in the form of HO—R'). The said substituents are linked with abnormal carbene through platinum by following the above procedure as described for Compound 4G'.

Synthesis of Compound 4H':

About 0.001 moles of chloride complex (Compound 4A) and $AgBF_4$ (about 0.002 moles) in about 5 ml DMSO/DCM (1:1) mixture are stirred for about 12 hours at room temperature. The mixture is filtered through celite; DCM is evaporated and lithium salt of cholesterol acid (prepared by the reaction of cholesterol with ethyl bromo acetate and then hydrolysis of the ester group by lithium hydroxide) (about 0.002 mole) in about 5 ml water is added and stirred at room temperature for about 24 hours. Compound 4H' separates out as precipitate which is thereafter filtered and washed with diethyl ether to get the pure Compound 4H'.

Synthesis of Compound 4H":

To obtain this compound, similar procedure is followed as described for the synthesis of Compound 4H'. However, about 0.002 moles of cholic acid or deoxycholic acid is being used instead of cholesterol acid derivative.

Synthesis of 4H:

Compound 4H is prepared by employing any other lipid containing a hydroxyl group which is converted to acid (in the form of COOH—$CH_2R'$). Said lipid is linked with abnormal carbene through platinum. Thereafter, the procedure as described for the synthesis of Compound 4H' is followed.

Note on platinum reaction: In an alternative path way, cyclooctadiene dichloro potassium [$Pt(Cl)_2(COD)$] is used as an alternative to potassium tetrachloro platinate [$K_2PtCl_4$] in above mentioned platinum complexation reaction

Example 5: (v) Synthesis of Abnormal NHC Platinum(II) Complexes Belonging to Compound 92 [Compounds 5A, 5B, 5C, 5C', 5D, 5D' and 5D" Respectively]

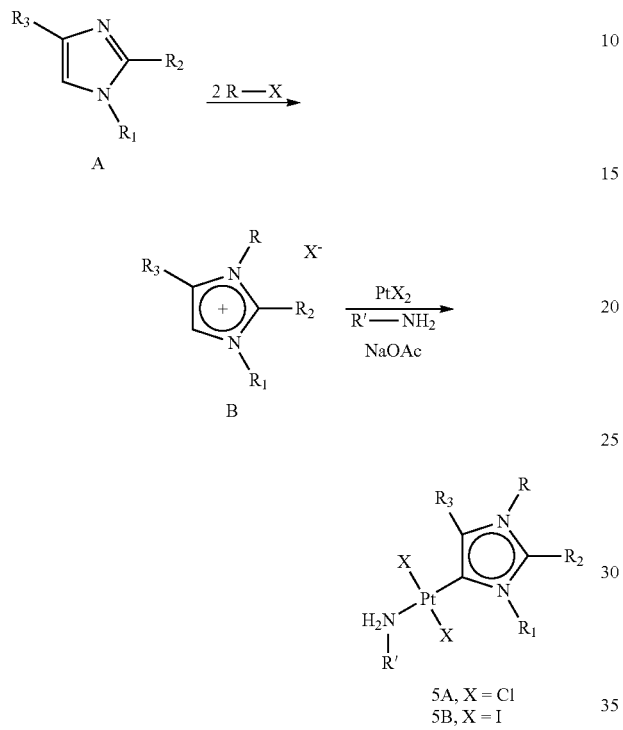

Synthesis of Compound B:

About 0.01 moles of 'A', 2-chloroethylamine or 2-iodoethylamine (about 0.03 moles) and potassium carbonate (0.01 moles) in about 5 ml of ethanol are stirred at about 25° C. for about 12 hours and then refluxed for about 6 hours. The reaction mixture is filtered and diethyl ether is added to give a precipitate of compound B.

Synthesis of Compounds 5A/5B (R'=Et, Pr, i-Pr):

About 0.001 moles of chloride/iodide salt (B), platinum chloride/platinum iodide (about 0.001 moles) and sodium acetate (about 0.002 moles) are mixed in alkyl amine (about 4 ml) and refluxed for about 6 hours. The reaction mixture is allowed to come down to room temperature. Amine is evaporated under reduced pressure and the compound is recrystallized from acetonitrile.

Synthesis of Compound 5C':

About 0.001 moles of cholesterol is treated with about 0.0012 moles of sodium hydride in THF and stirred at RT for about 12 hours. The solvent is evaporated and DMSO solution of residue (about 1 ml) is added to the DMSO (about 5 ml) solution of about 0.001 moles of Compound 5A. The mixture is stirred for about 24 hours at about 100° C. DCM is added to the reaction mixture to obtain the precipitate of Compound 5C'.

Synthesis of Compound 5C:

This compound is obtained by employing any other lipid or primary/secondary alcohols containing a hydroxyl group (in the form of HO—R') followed by linking with abnormal carbene through platinum and following the above procedure as described for Compound 5C'.

Synthesis of Compound 5D':

About 0.001 mole of chloride complex (Compound 5A) and AgBF4 (about 0.002 moles) in about 5 ml DMSO/DCM (1:1) mixture are stirred for about 12 hours at room temperature. The mixture filtered through celite; DCM is evaporated and lithium salt of cholesterol acid (prepared by the reaction of cholesterol with ethyl bromo acetate and then hydrolysis of the ester group by lithium hydroxide) (about 0.002 mole) in about 5 ml water is added and stirred at room temperature for about 24 hours. The Compound 5D' separates out as precipitate which is thereafter filtered and washed with diethyl ether to obtain the pure compound 5D'.

Synthesis of Compound 5D":

Similar procedure is followed as described in the synthesis of Compound 5D'. About 0.002 moles of cholic acid or deoxycholic acid is used instead of cholesterol acid derivative.

Synthesis of Compound 5D:

Any other lipid containing hydroxyl group which can be converted to acid (in the form of COOH—CH2R') is linked with abnormal carbene through platinum by following the above procedure as described for the synthesis of Compound 5D'.

Example 6: (vi) Synthesis of Abnormal NHC Platinum(II) Complexes Belonging to Compound 93 [Compounds 6A, 6B, 6C, 6C', 6D, 6D' and 6D" Respectively]

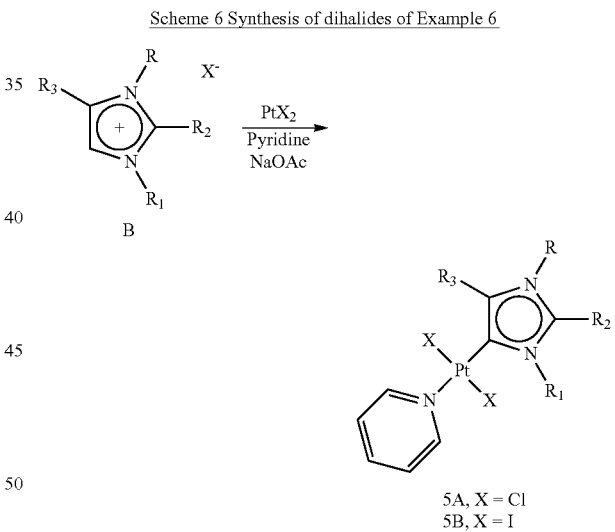

Synthesis of Compounds 6A/6B:

About 0.001 moles of chloride/iodide salt (B), platinum chloride/platinum iodide (about 0.001 moles) and sodium acetate (about 0.002 moles) are mixed in pyridine (about 3 ml) and stirred at about 20° C. for about 24 hours. Pyridine is evaporated under reduced pressure and the compound is recrystallized from acetonitrile.

Synthesis of Compound 6C':

About 0.001 moles of cholesterol is treated with about 0.0012 moles of sodium hydride in THF and stirred at RT for about 12 hours. The solvent is evaporated and DMSO solution of residue (about 1 ml) is added to the DMSO (about 5 ml) solution of about 0.001 moles of Compound 6A. The mixture is stirred for about 24 hours at about 100°

C. DCM is added to the reaction mixture to obtain the precipitate of the compound 6C'.

Synthesis of Compound 6C:

Any other lipid or primary/secondary alcohols which contain a hydroxyl group (in the form of HO—R') are linked with abnormal carbene through platinum by following the procedure as described for the synthesis of Compound 6C'.

Synthesis of Compound 6D':

About 0.001 moles of chloride complex (Compound 6A) and $AgBF_4$ (about 0.002 moles) in about 5 ml DMSO/DCM (1:1) mixture are stirred for about 12 hours at room temperature. The mixture is filtered through celite; DCM is evaporated and lithium salt of cholesterol acid (prepared by the reaction of cholesterol with ethyl bromo acetate and then hydrolysis of the ester group by lithium hydroxide) (about 0.002 moles) in about 5 ml water is added and stirred at room temperature for about 24 hours. Compound 6D' separates out as precipitate which is thereafter filtered and washed with diethyl ether to obtain the pure Compound 6D'.

Synthesis of Compound 6D":

Similar procedure is followed as mentioned in the synthesis of Compound 6D'. About 0.002 moles of cholic acid or deoxycholic acid is used instead of cholesterol acid derivative.

Synthesis of 6D:

Any other lipid which contain a hydroxyl group and can be converted to acid (in the form of COOH—$CH_2R'$) is linked with abnormal carbene through platinum by following the above procedure as described for the synthesis of Compound 6D'.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A compound of Formula (I):

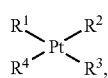

(I)

wherein:

$R_1$, $R_2$, $R_3$, $R_4$ are independently halogen, alkyl, amino, alkylamino, dialkylamino, hydroxyl, alkoxy, thiol, thioalkyl, O-acyl, chelated or non-chelated dicarboxylato linkage, or -linker-lipid or any combination thereof, provided that at least one of $R_1$, $R_2$, $R_3$, and $R_4$ is a N-heterocyclic carbene, wherein the carbene is an abnormal carbene and wherein the Pt atom is attached to a carbon in the N-heterocyclic carbene.

2. The compound of claim 1, wherein at least one of $R_1$, $R_2$, $R_3$ or $R_4$ is a -linker-lipid.

3. The compound of claim 2, wherein the platinum atom is conjugated to said lipid via covalent bond, coordinate bond or a combination thereof.

4. The compound of claim 2, wherein the linker is selected from the group consisting of:

(i) —X—$CH_2$—$X_2$—$X_1$—, wherein X is NH; $X_1$ is C(O)O, C(O)NH, O($CH_2$)—O, NH, or O; $X_2$ is $(CH_2)_n$ or C(O); and n is 0, 1, 2, 3, 4, or 5;

(ii) —$(CH_2)_n$O—, —$(CH_2)_n$NHC(O)O—, —$(CH_2)_n$OC(O)NH—, —$(CH_2)_n$C(O)NH$(CH_2)_m$O—, —$(CH_2)_n$O$(CH_2)_m$O—, —$(CH_2)_n$O(O)—, —$(CH_2)_n$NHC(O)$(CH_2)_m$O—, or —$(CH_2)_n$C(O)O—; wherein n and m are independently 0, 1, 2, 3, 4, or 5;

(iii) —$X_3$—$X_4X_5$—$X_6$—, wherein $X_3$ is CH, $CH_2$, or O; and $X_4$, $X_5$ and $X_6$ are independently same or different and are —$CH_2$O— or O; and (iv) any combinations of (i)-(iii).

5. The compound of claim 2, wherein the linker is selected from the group consisting of: a bond, ethylene diamine, ethylene glycol, diethylene glycol, 1,3-propanediol, glycine, beta alanine, —O—, —$CH_2$O—NHCH$_2$CH$_2$NHC(O)—, —NHCH$_2$CH$_2$NHC(O)O—, —NHCH$_2$CH$_2$—, —NHCH$_2$CH$_2$O—, —NHCH$_2$C(O)—, —NHCH$_2$C(O)O—, —NHCH$_2$C(O)OCH$_2$CH$_2$CH$_2$—, —NHCH$_2$C(O)OCH$_2$CH$_2$CH$_2$O—, —NHCH$_2$C(O)NH—, —CH$_2$CH$_2$—, —CH$_2$CH$_2$O—, —CH$_2$CH$_2$NHC(O)—, —CH$_2$CH$_2$NHC(O)O—, —CH$_2$CH$_2$O—, —CH$_2$C(O)NHCH$_2$CH$_2$—, —CH$_2$C(O)NHCH$_2$CH$_2$O—, —CH$_2$CH$_2$OCH$_2$CH$_2$—, —CH$_2$CH$_2$OCH$_2$CH$_2$O—, —CH$_2$C(O)—, —CH$_2$C(O)O—, —CH$_2$CH$_2$CH$_2$—, —CH$_2$CH$_2$CH$_2$O—, =CH—CH=CH$_2$—, =CH—CH=CHCH$_2$O—, —CH=CHCH$_2$—, —CH=CHCH$_2$O—, —OCH$_2$CH$_2$O—, —CH$_2$—, —CH$_2$O—, —NHC(O)CH$_2$—, —NHC(O)CH$_2$O—, —C(O)CH$_2$—, —C(O)CH$_2$O—, —OC(O)CH$_2$—, —OC(O)CH$_2$O—, —C(O)CH$_2$CH$_2$C(O)NHCH$_2$CH$_2$—, —OC(O)CH$_2$CH$_2$C(O)NHCH$_2$CH$_2$—, —C(O)CH$_2$CH$_2$C(O)NHCH$_2$CH$_2$O—, —OC(O)CH$_2$CH$_2$C(O)NHCH$_2$CH$_2$O—, —C(O)CH$_2$CH$_2$C(O)NHCH$_2$CH$_2$NHC(O)—, —OC(O)CH$_2$CH$_2$C(O)NHCH$_2$CH$_2$NHC(O)—, —C(O)CH$_2$CH$_2$C(O)NHCH$_2$CH$_2$NHC(O)O—, —OC(O)CH$_2$CH$_2$C(O)NHCH$_2$CH$_2$NHC(O)O—, and any combinations thereof.

6. The compound of claim 2, wherein the lipid is selected from the group consisting of fats, waxes, sterols, steroids, bile acids, fat-soluble vitamins, monoglycerides, diglycerides, phospholipids, glycolipids, sulpholipids, aminolipids, chromolipids, glycerophospholipids, sphingolipids, prenol lipids, saccharolipids, polyketides and fatty acids or any combination thereof, preferably sterols selected from cholesterol, cholesterol chloroformate or derivatives thereof, and any combination thereof.

7. The compound of claim 6, wherein the lipid is cholesterol or alpha-tocopherol.

8. A compound selected from the group consisting of Compound 86, Compound 87, Compound 88, Compound 90, Compound 91, Compound 92, Compound 93 and Compound 94:

Compound 86

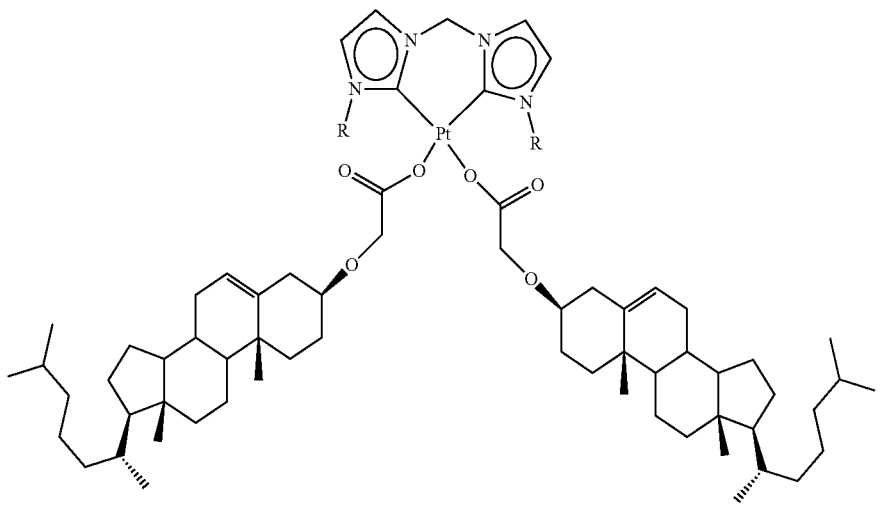

wherein each R is independently alkyl or substituted alkyl;

Compound 87

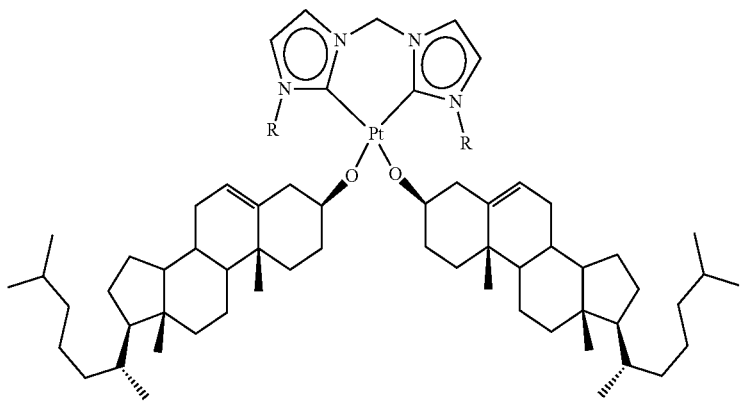

wherein each R is independently alkyl or substituted alkyl;

Compound 88

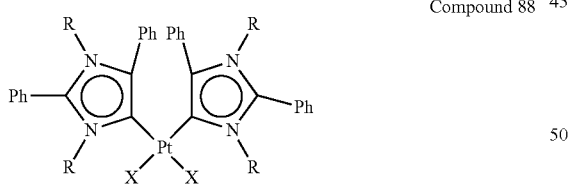

wherein each X is selected from independently from halide, chelated/non-chelated dicarboxylato linkage group or a combination thereof, and each R is independently alkyl or substituted alkyl;

Compound 90

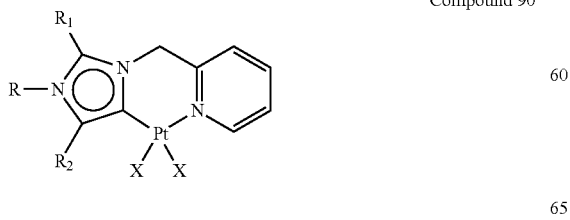

wherein each X is selected from independently from halide, chelated/non-chelated dicarboxylato linkage group or a combination thereof, and each of R, $R_1$ and $R_2$ are independently alkyl or substituted alkyl or phenyl or substituted phenyl;

Compound 91

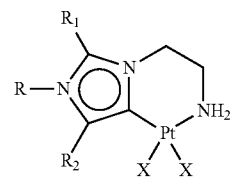

wherein each X is selected from independently from halide, chelated/non-chelated dicarboxylato linkage group or a combination thereof, and each of R, $R_1$ and $R_2$ are independently alkyl or substituted alkyl or phenyl or substituted phenyl;

Compound 92

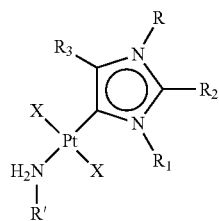

wherein each X is halide and each of R, $R_1$, $R_2$ and $R_3$ are independently alkyl or substituted alkyl or phenyl or substituted phenyl;

Compound 93

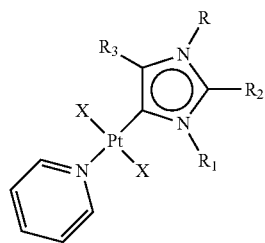

wherein each X is halide and each of R, $R_1$, $R_2$ and $R_3$ are independently alkyl or substituted alkyl or phenyl or substituted phenyl;

Compound 94

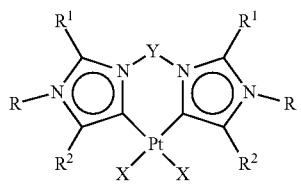

wherein each X is selected independently from halide, chelated/non-chelated dicarboxylato linkage group or a combination thereof, and each of R, $R_1$ and $R_2$ are independently alkyl or substituted alkyl or phenyl or substituted phenyl, and Y is selected from the group consisting of $CH_2$, $CH_2$—$CH_2$ and CO.

9. A nanoparticle comprising a platinum compound of claim 1.

10. The nanoparticle of claim 9, wherein the nanoparticle further comprises a co-lipid and/or stabilizer.

11. The nanoparticle of claim 10, wherein ratio of the compound to co-lipid and/or stabilizer ranges from 99:1 to 1:99 (w/w), (mol/mol) or (vol/vol).

12. The nanoparticle of claim 11, wherein the nanoparticle comprises Soy-phosphatidyl choline and 1,2-Distearoyl-sn-Glycero-3-Phosphoethalonamine-N-[Methoxy(Polyethylene glycol)-2000] as co-lipids, and wherein the ratio of the compound and the co-lipids ranges from about 1:1:0.01 to about 1:4:3.

* * * * *